United States Patent [19]

Shimizu et al.

[11] Patent Number: 4,808,711

[45] Date of Patent: Feb. 28, 1989

[54] CEPHALOSPORIN DERIVATIVES

[75] Inventors: Shigeo Shimizu; Hiroyuki Takano; Fujio Yagihashi, all of Mukawa, Japan

[73] Assignees: Sankei Pharmaceutical Co., Ltd.; Nippon Pharmaceutical Development Institute Co., both of Tokyo, Japan

[21] Appl. No.: 819,831

[22] Filed: Jan. 17, 1986

[30] Foreign Application Priority Data

Jan. 21, 1985 [JP] Japan .................................. 60-8587
Jan. 25, 1985 [JP] Japan .................................. 60-11986

[51] Int. Cl.[4] .................. C07D 501/36; A61K 31/545
[52] U.S. Cl. .................... 540/227; 540/225; 540/222
[58] Field of Search .............. 540/221, 225, 222, 227

[56] References Cited

U.S. PATENT DOCUMENTS 4,200,575  4/1980  Numata et al. ................... 540/225

FOREIGN PATENT DOCUMENTS 150507  8/1985  European Pat. Off. .

Primary Examiner—Nicholas S. Rizzo
Attorney, Agent, or Firm—Antonelli, Terry & Wands

[57] ABSTRACT

There is disclosed a novel β-lactam antibiotics represented by the formula:

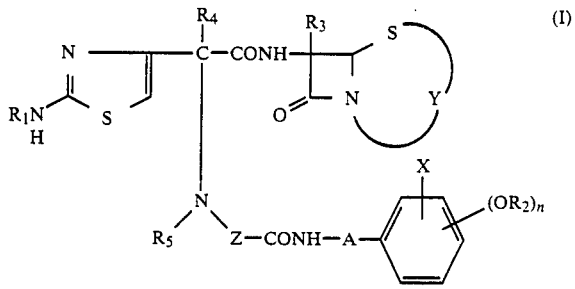

wherein A is a group represented by the formulae $-NHCO-$, $-NHCONHCO-$, $-NHCOCH=CH-$ or

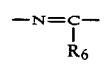

where $R_6$ is a hydrogen atom or a lower alkyl group; $R_1$ and $R_2$ are independently a hydrogen atom or a protective group; $R_3$ is a hydrogen atom or a methoxy group; X is a hydrogen atom, a hydroxyl group, a protected hydroxyl group, a halogen atom, a lower alkoxy group or a nitro group; n is an integer of 1 or 2; Y is a group represented by the formulae:

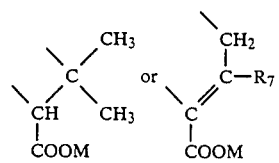

provided that a carbon atom which is bonded by a carboxyl group being bonded to nitrogen atom; M is a hydrogen atom, a protective group or an easily hydrolyzable group in a human body; $R_7$ is a hydrogen atom, a methyl group a lower alkoxy-methyl group or a group represented by the formula: $-CH_2-T$ where T is an acyloxy group, a carbamoyloxy group, a quaternary ammonium, a substituted or unsubstituted heterocyclic ring or a formula: $-S-R_8$ where $R_8$ is an acyl group or a substituted or unsubstituted heterocyclic ring, $R_4$ and $R_5$ are each hydrogen atoms or combined with each other to form additional direct bond; Z is a direct bond or a carbonyl group when $R_4$ and $R_5$ are hydrogen atoms, or a formula: $-O-B-$ where the oxygen atom is bonded to nitrogen atom and B is a straight, branched or cyclic alkylene group when $R_4$ and $R_5$ are combined with each other to form additional direct bond, or its pharmaceutically acceptable salt.

9 Claims, No Drawings

CEPHALOSPORIN DERIVATIVES

BACKGROUND OF THE INVENTION

This invention relates to a novel β-lactam antibiotics, more particularly to a novel penicillin series and cephalosporin series antibiotics.

Heretofore, it has been known that a β-lactam series antibiotics has antibacterial activities to gram positive bacteria and gram negative bacteria and many of these compounds have actually been applied therefor. Among them, compounds which are called to as the third aged cephalosporin series antibiotics have wide range of antibacterial spectrum and particularly are evaluated in the clinical field.

However, while the several kinds of the above compounds have been used in practical use, all of them are inferior in their antibiotical activities to Pseudomonas aeruginosa. Further, some kinds of them are finely effective to gram negative bacteria other than Pseudomonas aeruginosa but they have a disadvantage of lower activities to gram positive bacteria.

SUMMARY OF THE INVENTION

The present inventors have intensively studied, by referring to the above situation, concerning a compound which has potent activities in extremely wide ranges, and as a result, have found that the compound represented by the formula (I) has potent activities to gram negative bacteria including *Pseudomonas aeruginosa* and *Serratia marcescens* and other pathogenic bacteria as well as gram positive bacteria and accomplished the present invention.

That is, the present invention comprises a β-lactam compound represented by the formula:

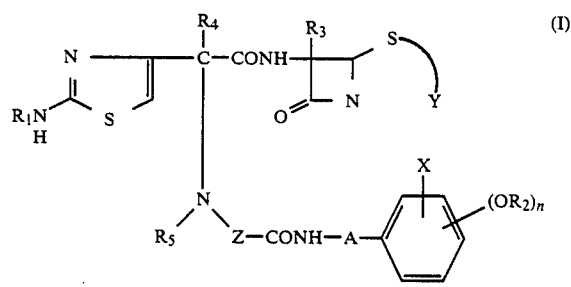

wherein

A is a group represented by the formulae —NHCO—, —NHCONHCO—, —NHCOCH=CH— or

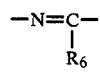

where $R_6$ is a hydrogen atom or a lower alkyl group; $R_1$ and $R_2$ are independently a hydrogen atom or a protective group, $R_3$ is a hydrogen atom or a methoxy group; X is a hydrogen atom, a hydroxyl group, a protected hydroxyl group, a halogen atom, a lower alkoxy group or a nitro group; n is an integer of 1 of 2; Y is a group represented by the formulae:

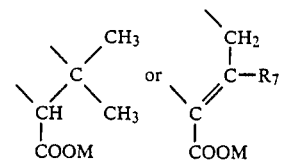

provided that a carbon atom which is bonded by a carboxyl group being bonded to nitrogen atom; M is a hydrogen atom, a protective group or an easily hydrolyzable group in a human body;

$R_7$ is a hydrogen atom, a methyl group a lower alkoxymethyl group or a group represented by the formula: —CH$_2$—T where T is an acyloxy group, a carbamoyloxy group, a quaternary ammonium, a substituted or unsubstituted heterocyclic ring or a formula: —S—R$_8$ where $R_8$ is an acyl group or a substituted or unsubstituted heterocyclic ring, $R_4$ and $R_5$ are each hydrogen atoms or combined with each other to form additional direct bond; Z is a direct bond or a carbonyl group when $R_4$ and $R_5$ are hydrogen atoms, or a formula: —O—B— where the oxygen atom is bonded to nitrogen atom and B is a straight, branched or cyclic alkylene group when $R_4$ and $R_5$ are combined with each other to form additional direct bond, or its pharmaceutically acceptable salt.

Further, these pharmaceutically acceptable salt, or hydrates or oranic solvates thereof are included in the scope of the present invention as a matter of course.

PREFERRED EMBODIMENTS OF THE INVENTION

Next, each groups which are summarily shown in the above formula (I) are explained in more detail.

Explanation of A

A is a group represented by the following formulae: —NHCO—, —NHCONHCO—, —NHCOCH=CH— or

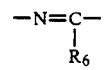

where $R_6$ is a hydrogen atom or a lower alkyl group. In the above, the lower alkyl group means straight or branched alkyl groups having 1 to 3 carbon atoms such as a methyl group, an ethyl group, an n- or iso-propyl group, etc.

Explanation of $R_1$

As a protective group, there may be mentioned a formyl group, a trityl group, a chloroacetyl group, a t-butoxycarbonyl group, a 2,2,2-trichloroethoxycarbonyl group, etc.

Explanation of $R_2$

As a protective group, there may be mentioned lower acyl groups such as an acetyl group, a proionyl group, etc.; or lower alkoxycarbonyl groups such as a methoxycarbonyl group, an ethoxycarbonyl group, etc.

Explanation of R₃

R₃ is a hydrogen atom or a methoxy group.

Explanation of R₄ and R₅

R₄ and R₅ are each hydrogen atoms or combined with each other to form additional direct bond, i.e., C and N in the formula are bonded with a double bond (C=N).

Explanation of X

In the X, as the protected hydroxyl group, there may be included acyloxy groups, etc. as explained in R₂. Further, the lower alkoxy group means alkoxy groups having 1 to 6 carbon atoms such as a methoxy group, an ethoxy group, an n-propoxy group, an isopropoxy group, an n-butoxy group, etc.

Explanation of Y

In the Y, R₇ represents a hydrogen atom, a methyl group, a lower alkoxymethyl group or a group represented by the following formula: —CH₂—T.

In the above, the lower alkoxymethyl group is alkoxymethyl groups having 2 to 7 carbon atoms such as a methoxymethyl group, an ethoxymethyl group, an n-propoxymethyl group, an isopropoxymethyl group, an n-butoxymethyl group, etc.

Further, T represents an acyloxy group, a carbamoyloxy group, a quaternary ammonium, a substituted or unsubstituted heterocyclic ring or the following formula: —S—R₈ (wherein R₈ is an acyl group or a substituted or unsubstituted 5- or 6-membered heterocyclic ring.).

In the above, as the acyloxy group, an acetoxy group, a propionyloxy group, etc. are preferred.

As the quaternary ammonium, preferred are pyridine, optionally substituted pyridines such as 2-methylpyridine, 3-methylpyridine, 4-methylpyridine, 4-ethylpyridine, 2,3-dimethylpyridine, 4-aminopyridine, 3-cyanopyridine, nicotinamide, isonicotinamide, 3-pyridine sulfonic acid, 4-pyridine ethanesulfonic acid, 3-hydroxypyridine, 4-hydroxypyridine, nicotinic acid, isonicotinic acid, 5,6,7,8-teterahydroisoquinoline, 5,6,7,8-tetrahydroquinoline and the like; aromatic cyclic nitrogen compounds such as pyridazine, quinoline, isoquinoline and the like; or quaternary ammoniums derived from aliphatic tertiary amines such as trimethylamine, triethylamine, N-methylpiperidine, N-methylpyrrolidine, N-methylmorpholine and the like.

In the above —S—R₈, as the acyl group of R₈, preferred are an acetyl group, a propionyl group, a furoyl group, etc.

Further, the substituted or unsubstituted 5- or 6-membered heterocyclic group as T or R₈ means all the heterocyclic compounds having 1 to 4 hetero atoms in the ring, which may have optional substituents in the hetero ring. There may be mentioned, for example, a tetrazolyl group, a triazolyl group, a thiazolyl group, a thiadiazolyl group, a tetrazolo[1,5-b]pyridazinyl group, a pyridyl group, an N-methylpyridyl group, an s-triazolo[1,5-a]pyrimidyl group, a 1-oxidopyridyl group, an N-carbamoylmethylpyridyl group, a 2-methyl-5-oxo-6-hydroxy-2,5-dihydro-1,2,4-triazinyl group, a 4-methyl-5-oxo-6-hydroxy-4,5-dihydroxy-1,2,4-triazinyl and the like, all of which may be substituted by a lower alkyl group, a lower alkoxy group, a carboxymethyl group, a carboxyethyl group, a sulfoxymethyl group, a sulfoxyethyl group, a di-lower-alkylaminoethyl group, a carboxy group, an amino group, an acetylamino group, a hydroxyethyl group and the like.

In —COOM, when the M is a protective group, there may be mentioned a diphenylmethyl group, a t-butyl group, a p-nitrobenzyl group, a trimethylsilyl group, etc.

Further, when the M is a group which is easily hydrolizable in a human body, there may be mentioned an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group, a 5-methyl-2-oxo-1,3-dioxol-4-ylmethyl group and the like.

Explanation of Z

When Z is a direct bond, N atom and C atom which are bonded to Z in the formula are directly bonded with each other.

Explanation of B

In the B, as the straight, branched or cyclic alkylene group, there may be mentioned those having 1 to 6 carbon atoms, for example, the following alkylene groups are preferred.

$$-CH_2-, \quad -CH_2-CH_2-, \quad \underset{CH_3}{-CH-}, \quad \underset{C_2H_5}{-CH-}, \quad \underset{C_3H_7}{-CH-},$$

$$\underset{CH_3}{\overset{CH_3}{-C-}} \quad \text{and} \quad \underset{CH_3}{\overset{CH_3}{-CH_2-C-}}$$

As the pharmaceutically acceptable salts of the β-lactam compounds according to the present invention, there may be mentioned alkali metal salts such as of sodium salts, potassium salts, etc.; alkaline earth metal salts such as of magnesium salts, calcium salts, etc.; ammonium salts; salts with organic bases such as of diisopropylamine, benzylamine, triethanolamine, triethylamine, N-methylmorpholine, pyridine, piperazine, etc.; salts with organic acids such as of acetic acid, formic acid, maleic acid, fumaric acid, methanesulfonic acid, p-toluenesulfonic acid, etc.; salts with inorganic acids such as of hydrochloric acid, hydrobromic acid, sulfuric acid, phosphoric acid and the like.

Manufacturing methods of the novel β-lactam compounds

The novel β-lactam compounds and derivatives thereof to be intended in the present invention can be produced, roughly be mentioned, according to the following three methods.

The first method

The title compound can be obtained by reacting the compound represented by the formula (II):

$$NH_2 \underset{O}{\overset{R_3}{\underset{\parallel}{\fbox{}}}} \overset{S}{\underset{N}{\fbox{}}} Y \quad (II)$$

wherein symbols in the formula are the same as mentioned above, with the carboxylic acid represented by the formula (III):

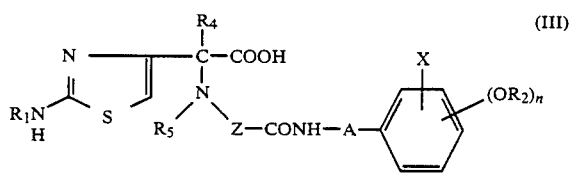

(III)

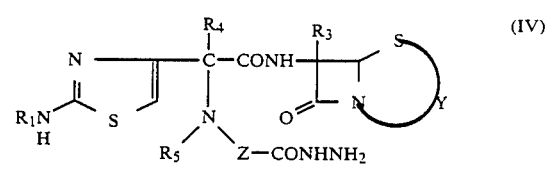

(IV)

wherein symbols in the formula are the same as mentioned above, or its reactive derivative and removing a protective group, if necessary.

In this method, the compound represented by the formula (III) which is used as a starting compound is a novel compound, and one of producing method or the title compound is shown by referring reaction schemes in the following:

wherein symbols in the formula are the same as mentioned above, with any one of compounds represented by the formulae:

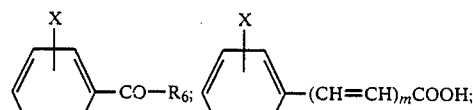

(a)

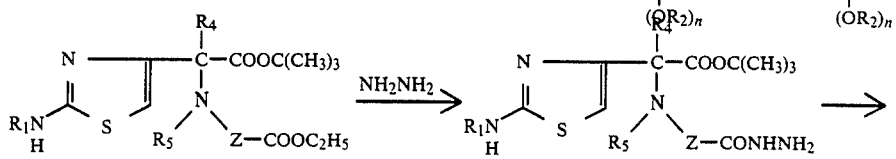

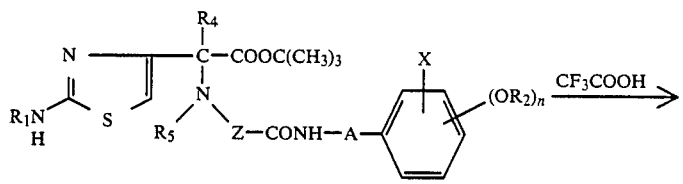

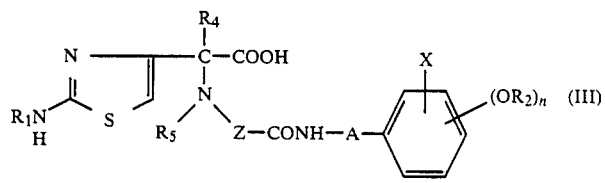

(III)

wherein symbols in the formula are the same as mentioned above.

(b)

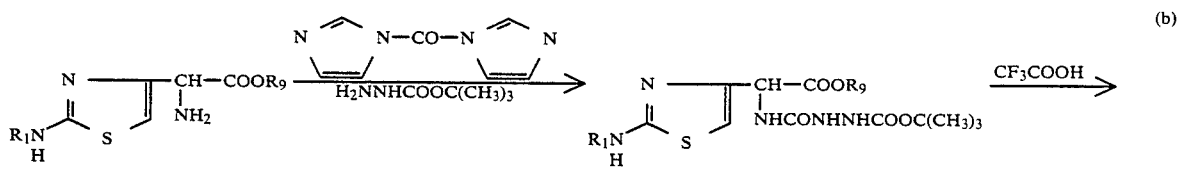

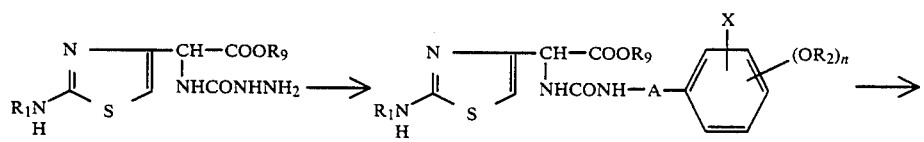

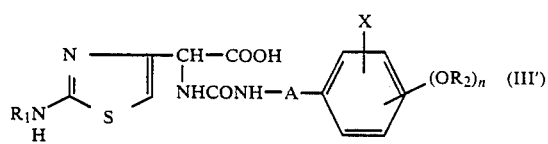

(III')

wherein $R_9$ is a lower alkyl group or an aryl group and the other symbols are the same as mentioned above.

The second method

The titel compound can be obtained by reacting the compound represented by the formula (IV):

-continued

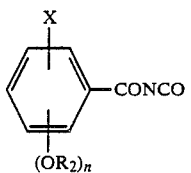

wherein m is an integer of 0 or 1, and the other symbols are the same as mentioned above, and removing a protective group, if necessary.

In this method, the starting compound represented by the formula (IV) is a novel compound, and an example of the producing method is shown by referring reaction schemes in the following:

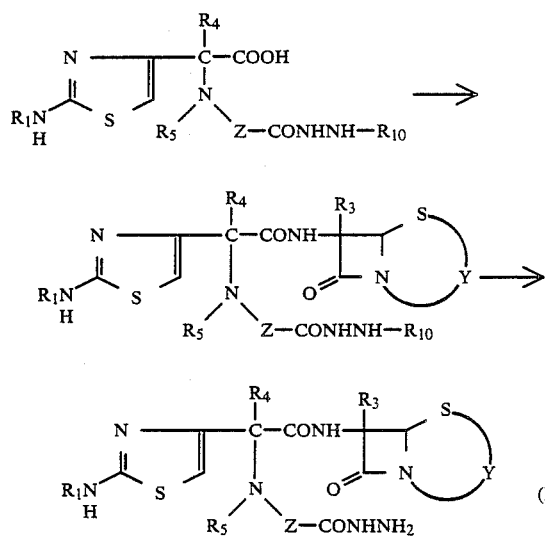

wherein $R_{10}$ is a protective group and the other symbols are the same as mentioned above.

The third method

The compound represented by the formula (I'):

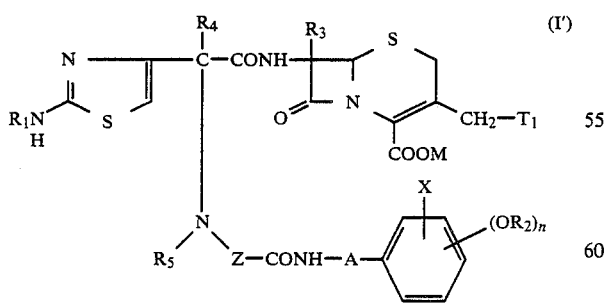

wherein $T_1$ represents a quaternary ammonium or $-R-R_8$ and the other symbols are the same as mentioned above, can be obtained by reacting the compound represented by the formula (V):

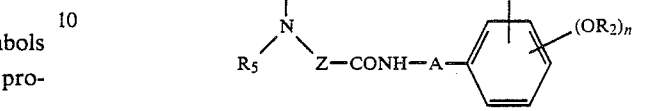

wherein J represents a halogen atom or an acetoxy group and the other symbols are the same as mentioned above, with a tertiary amine or $R_8-SH$ and by removing the protective group if necessary.

In the following, producing methods of the novel β-lactam antibiotics according to the present invention will be explained in more detail.

The first method

The reaction between the compound (II) and the compound (III) should desirably be carried out, in general, by using reactive derivatives of the compound (III) as the compound (III). As the reactive derivatives, there may be mentioned, for example, acid halides, mixed acid anhydrides, active esters and the like. Further, while free carboxylic acids can be used as such, suitable condensation reagent may desirably be used in this case. As the reagent, there may be employed, for example, N,N'-dicyclohexylcarbodiimide (DCC), N,N'-carbonyldiimidazole, cyanuric chloride, Vilsmeier reagent and the like. Such reactions have been known in the field of penicillin chemistry, cephalosporin chemistry and peptide chemistry.

These reactions are usually carried out in a suitable solvent such as dichloromethane, chloroform, tetrahydrofuran, dioxane, dimethylformamide, dimethylacetamide, acetonitrile, acetone, water or mixed solvents of the above. Treatments after the reaction can be carried out by the methods well known in the art such as separation, purification and the like.

The second method

The reaction of the compound (IV) and

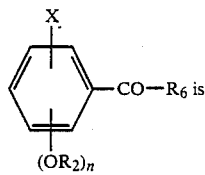

carried out by reacting them in water, methanol or ethanol at about 10° to 50° C. and the terminal point of the reaction is confirmed by a thin layer chromatography. The reaction time is about 0.5 to 48 hours.

In case of employing

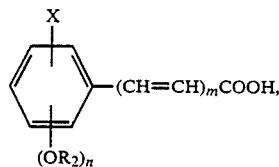

it can be reacted as acid halides, mixed acid anhydrides or active esters, or suitable condensation reagents such as N,N'-dicyclohexylcarbodiimide (DDC), N,N'-carbonyldiimidazole, cyanuric chloride, Vilsmeier reagent and the like can be employed. These reactions can be carried out at about −10° to 20° C. for about 0.5 to 2 hours.

In case of employing

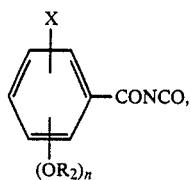

the reaction can easily be proceeded in an inert solvent such as dimethylformamide, dimethylactamide, dimethylsulfoxide, dichloromethane, chloroform, acetonitrile or a mixed solvent of the above at about 0° to 50° C. The terminal point of the reaction should be confirmed by a thin layer chromatography. The reaction time is about 0.5 to 6 hours.

The thus obtained compound (I) can be easily separated and purified by the known method.

The third method

When the compound (V) and a tertiary amine are reacted, the reaction is carried out in water in case of —COOM being a free carboxylic acid or a its salt, and a catalyst is used if necessary. As the catalyst, there may be employed, for example, potassium thiocyanate, sodium thiocyanate, potassium bromide sodium bromide and the like. The reaction is carried out at a temperature of 20° to 80° C. and the terminal point of the reaction is confirmed by a thin layer chromatography. The reaction time is about 1 to about 24 hours.

In case of —COOM being ester and J being a halogen atom, the reaction is carried out by contacting a tertiary amine in an organic solvent. However, a part of the double bonds will transfer whereby isomer will likely be generated.

The reaction of the compound (V) and R$_8$—SH is carried out by contacting them in water or a water-soluble organic solvent such as acetone, methanol, ethanol, isopropanol, acetonitrile, etc. when—COOM is a free carboxylic acid or its salt. This reaction is desirably carried out at around neutral of pH and the reaction system can be maintained at around neutral by properly adding alkaline compounds such as an alkali hydroxide, an alkali carbonate, an alkali hydrogencarbonate, an alkali dihydrogenphosphate, an alkali monohydrogenphosphate, etc. The reaction temperature is generally about 20° to 70° C. The terminal point of the reaction is confirmed by a thin layer chromatography. The reaction time is about 1 to 24 hours. Since the thus obtained compound (I') is being dissolved as a water-soluble alkali salt in a reaction mixture, it can be carried out an adsorption, separation and purification by using adsorptive resins such as Diaion HP-20 (trade name, produced by Mitsubishi Kasei Co.), Amerlite XAD II (trade name, produced by Rohm & Haas, Co.), etc.

In the present invention, the compound (I) obtained each methods of (1), (2) and (3) as mentioned above can be converted into, if necessary, a pharmaceutically acceptable salt or an ester which is easily hydrolized in a human body when the compound has a free carboxylic acid.

Thus, the compound of formula (I) obtained according to the present invention has high antibacterial activity as well as no toxicity at an effective dosage (LD$_{50}$ value is 5 g/kg or more when intravaneous administration to mouse is carried out) and thus it is an effective compound as a medicine. For example, it shows excelleent antibacterial activity against a wide range of pathogenic bacteria such as gram negative bacteria including *Pseudomonas aeruginosa* and gram positive bacteria.

Accordingly, the β-lactam compound according to the present invention can be effectively utilized for the sake of prevention or remedy of diseases due to the aforesaid pathogenic bacteria in human beings or animals.

The β-lactam compound according to the present invention can be administrated orally or non-orally to human beings or animals by various administrating method.

Further, said derivatives are used singly or formulating with auxiliaries, liquid diluents, binders, lubricants, humectants, etc., for example, in the form of general medicinal compositions such as tablets, granulars, sugar coating tablets, powder, capsules, gels, dry syrup, syrup, amples, suspension, liquid, emulsion, ointments, paste, cream, suppositorys, etc.

Moreover, as the other additives which can be formulated, there may be mentioned dissolution delaying agents, absorption accelerating agents, surface active agents, etc. Any way, forms which are pharmaceutially acceptable one can be employed.

The β-lactam compound according to the present invention can be used as alone or mixture of two or more different kinds of derivatives and the amount of the compounds is about 0.1 to 99.5%, preferably 0.5 to 95% based on the weight of the all medicinal composition.

The medicinal composition according to the present invention can be formulated an other compounds which are pharmaceutically active as effective ingredients other than said novel β-lactam compound or mixtures thereof.

A dosage per day to a patient of the novel β-lactam compound according to the present invention may be varied depending upon an individual man, kinds of animals, weights thereof and a state to be remedied, but generally is in the range of 1 to 1000 mg per 1 kg of weight, preferably about 10 to 800 mg.

In the following, the present invention is eplained in detail by referring Examples.

REFERENCE EXAMPLE 1

Synthesis of 7-[2-(2-amino-1,3-thiazol-4-yl)-2-carbozoylmethoxyiminoacetamido]-3-acetoxymethyl-3-cephem-4-carboxylic acid diphenylmethyl ester.dihydrochloride Afer colling 40 ml of methanol, 1.53 g (10 mmole) of phosphorus oxychloride was added thereto and then to the mixture was added 3.4 g (4.62 mmole) of 7-[2-(2-formylamino-1,3-thiazol-4-yl)-2-(3-formylcarbazoyl)methoxyiminoacetamido]-3-acetoxymethyl-3-cephem-4-carboxylic acid diphenylmethyl ester and stirred for one hour under ice-cooling. The resuling mixture was added dropwise into 400 ml of ether while vigorously stirring and resulting precipitates were collected by filtration and dried to obtain 2.91 g of the title compound. (Yield: 83.7%)

Structural formula:

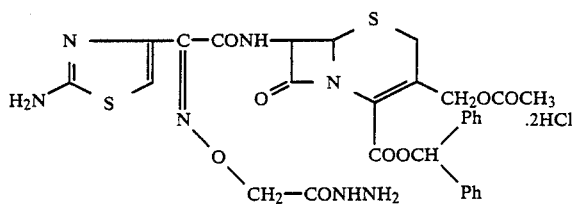

$^1$H NMR (d$_6$-DMSO) δ: 1.96 (s, 3H), 3.67 (s, 2H), 4.81 (s, 2H), 5.22 (d, 1H), 5.72–6.10 (m, 1H), 6.90 (s, 1H), 7.33 (s, 10H).

REFERENCE EXAMPLES 2 to 7

In the same manner as in Reference example 1, dihidrochlorides of the compounds shown below can be obtained. The results are shown in Table 1.

REFERENCE EXAMPLE 8

Synthesis of 7-[2-(2-amino-1,3-thiazol-4-yl)-2-carbozoylmethoxyiminoacetamido]-3-acetoxymethyl-3-cephem-4-carboxylic acid·dihydrochloride To an ice-cooled mixture comprising 24 ml of trifluoroacetic acid and 6 ml of anisole was added 2.45 g (3.25 mmole) of the compound obtained in Reference example 1 and stirred for 30 minutes under ice-cooling. The resulting mixture was added dropwise into 500 ml of ether while vigorously stirring and resulting precipitates were collected by filtration and dried to obtain 1.81 g of the title compound. (Yield: 95%)

Structural formula:

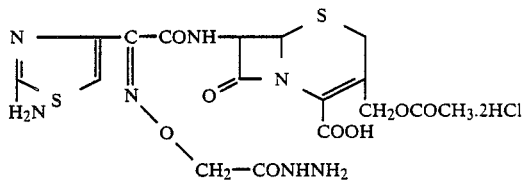

$^1$H NMR (d$_6$-DMSO)δ: 2.03 (s, 3H), 3.72 (broad s, 2H), 4.80 (s, 2H), 5.17 (d, 1H), 5.63–6.05 (m, 1H), 7.03 (s, 1H).

TABLE 1

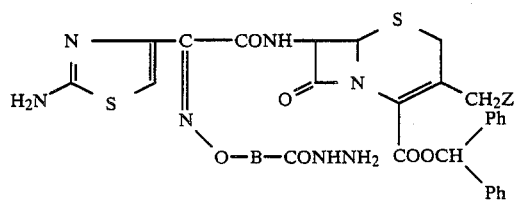

| Reference example | B | Z | Yield (%) | Melting point (°C.) | $^1$H NMR (d$_6$-DMSO)δ |
|---|---|---|---|---|---|
| 2 | —CH$_2$— | ![triazole with N-CH$_3$] | 79.5 | 150–156 (decomposed) | 3.78(broad s, 2H), 3.82(s, 3H), 4.12~4.41(m, 2H), 4.65(broad s, 2H), 5.23(d, 1H), 5.75–6.13(m, 1H), 6.80(s, 1H), 7.27(s, 10H) |
| 3 | —CH$_2$— | ![thiadiazole-CH$_3$] | 98.0 | 142~149 (decomposed) | 2.65(s, 3H), 3.80(broad s, 2H), 4.39(m, 2H), 4.82(s, 2H), 5.26(d, 1H), 5.76~6.10(m, 1H), 6.90(s, 1H), 7.40(s, 10H) |
| 4 | —CH$_2$— | ![thiadiazole] | 63.5 | 110~118 (decomposed) | 3.75(broad s, 2H), 4.36(m, 2H), 4.71(s, 2H), 5.27(d, 1H), 5.83~6.17(m, 1H), 6.94(s, 1H), 7.38(s, 10H), 9.50(s, 1H) |
| 5 | —CH— \| CH$_3$ | ![thiadiazole] | 80.8 | | 1.45(d, 3H), 3.75(broad s. 2H), 4.35(m, 2H), 4.87(q, 1H), 5.23(d, 1H), 5.74~6.07(m, 1H), 6.87(s, 1H), 7.33(s, 10H), 9.52(s, 1H) |
| 6 | CH$_3$ \| —C— \| CH$_3$ | ![thiadiazole] | 76.8 | | 1.56(s, 6H), 3.78(broad s, 2H), 4.40(m, 2H), 5.26(d, 1H), 5.72~6.05(m, 1H), 6.90(s, 1H), 7.36(broad s, 10H), 9.56(s, 1H) |
| 7 | —CH$_2$— | H | 84.2 | 126–130 (decomposed) | 2.12(s, 3H), 3.54(broad s, 2H), 4.88(broad s, 2H), 5.16(d, 1H), 5.60~5.93(m, 1H), 6.87(s, 1H), 7.13~7.62(s, 10H) |

REFERENCE EXAMPLES 9 TO 11

In the same manner as in Reference example 8, dihydrides of the compounds represented by the following formulae were synthesized from the compounds obtained in Reference examples 3, 4 and 5, respectively. The results are shown in Table 2.

EXAMPLE 2

Synthesis of 7-{2-[2-amino-1,3-thiazol-4-yl]-2-[3-(3,4-dihydroxybenzylidene)carbazoyl]methoxyiminoacetamido}-3-[(1-methyl-1,2,3,4-tetrazol-5-yl)thiomethyl]-3-cephem-4-carboxylic acid.hydrochloride

TABLE 2

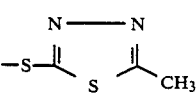

| Reference example | B | Z | Yield (%) | Melting point (°C.) | $^1$H NMR (d$_6$-DMSO)δ |
|---|---|---|---|---|---|
| 9 | —CH$_2$— | 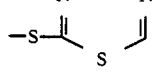 | 96 | 145~150 (decomposed) | 2.70(s, 3H), 3.74(broad s, 2H), 4.40(m, 2H), 4.82(s, 2H), 5.20(d, 1H), 5.65~5.98(m, 1H), 7.08(s, 1H) |
| 10 | —CH$_2$— | | 93 | 148~152 (decomposed) | 3.74(broad s), 4.38(m, 2H), 4.73(s, 2H), 5.26(d, 1H), 5.85~6.16(m, 1H), 6.95(s, 1H), 9.55(s, 1H) |
| 11 | —CH— \| CH$_3$ | | 95 | 172~176 (decomposed) | 1.48(d, 3H), 3.77(s, 2H), 4.47(m, 2H), 4.87(q, 1H), 5.22(d, 1H), 5.65~6.06(m, 1H), 7.10(s, 1H), 9.65(s, 1H) |

EXAMPLE 1

Synthesis of 7-{2-[2-amino-1,3-thiazol-4-yl]-2-[3-(3,4-dihydroxybenzylidene)carbazoyl]methoxyiminoacetamido}-3-acetoxymethyl-3-cephem-4-carboxylic acid.hydrochloride In 10 ml of methanol were dissolved 0.88 g (1.5 mmole) of 7-[2-(2-amino-1,3-thiazol-4-yl)-2-carbozoylmethoxyiminoacetamido]-3-acetoxymethyl-3-cephem-4-carboxylic acid.dihydrochloride obtained in Reference example 8 and 0.249 g (1.8 mmole) of 3,4-dihydroxybenzaldehyde and the mixture was stirred at room temperature for one hour. The resulting mixture was added dropwise into 200 ml of ether while vigorously stirring and resulting precipitates were collected by filtration, washed with ether and then dried to obtain 0.85 g of the title compound. (Yield: 84.6%)

Structural formula:

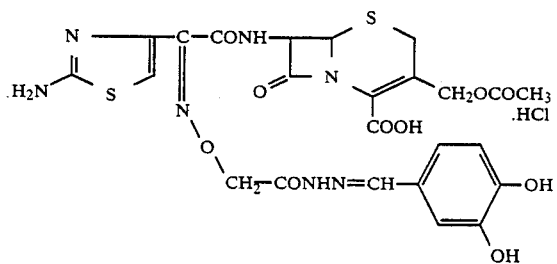

$^1$H NMR (d$_6$-DMSO)δ: 2.06 (s, 3H), 3.62 (broad s, 2H), 4.82 (s, 2H), 5.25 (d, 1H), 5.80–6.05 (m, 1H), 6.90 (d, 1H), 6.85–7.30 (m, 3H), 8.01 (d, 1H).

(I) In 10 ml of methanol were dissolved 0.485 g (0.6 mmole) of 7-[2-(2-amino-1,3-thiazol-4-yl)-2-carbozoylmethoxyiminoacetamido]-3-[(2-methyl-1,2,3,4-tetrazol-5-yl)thiomethyl]-3-cephem-4-carboxylic acid diphenylmethyl ester.dihydrochloride and 0.10 g (0.72 mmole) of 3,4-dihydroxybenzaldehyde and the mixture was stirred at room temperature for one hour.

The resulting mixture was added dropwise into 150 ml of ether while vigorously stirring and resulting precipitates were collected by filtration, washed with ether and then dried to obtain 0.51 g of diphenylmethyl ester of the title compound. (Yield: 95.2%)

(II) To the ice-cooled mixture comprising 4 ml of trifluoroacetic acid and 1 ml of anisole was added 0.28 g (0.314 mmole) of the above diphenylmethyl ester and the mixture was stirred for 30 minutes. Thereafter, the resulting mixture was added dropwise into 100 ml of ether while vigorously stirring and resulting precipitates were collected by filtration, washed with ether and dried to obtain 0.22 g of the title compound. (Yield: 98%)

Melting point: 131° to 136° C. (decomposed).
Structural formula:

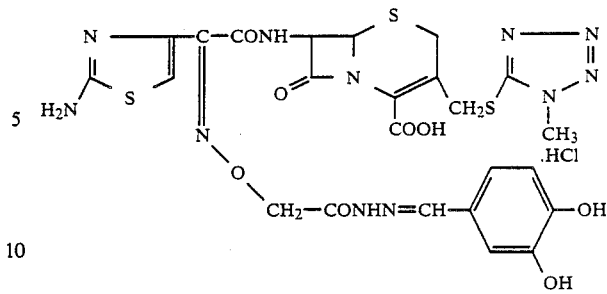
$^1$H NMR (d$_6$-DMSO)δ: 3.75 (broad s, 2H), 3.95 (s, 3H), 4.23 (m, 2H), 4.63 (broad s, 2H), 5.16 (d, 1H), 5.75–6.13 (m, 1H), 6.80 (d, 1H), 6.83–7.43 (m, 3H), 8.01 (d, 1H).
EXAMPLES 3 TO 33
In the same manner as in Example 1, hydrochlorides of the β-lactam compounds represented by the following formula were prepared. The results are shown in Table 3.

TABLE 3

Structure (header):

$H_2N$-[thiazole]-C(=N-O-B-CONHN=C(Q_1)(Q_2))-CONH-[β-lactam with S]-CH_2-Z, COOH

| Example | B | Z | $Q_1$ | $Q_2$ | Yield (%) | Melting point (°C.) | 1H NMR ($d_6$-DMSO)δ |
|---|---|---|---|---|---|---|---|
| 3 | —CH$_2$— | —S—[N=N, CH$_3$ thiadiazole] | 3-hydroxyphenyl (m-OH) | H | 72.7 | 157~160 (decomposed) | 2.68(s, 3H), 3.72(s, 2H), 4.42(m, 2H), 4.84(broad s, 2H), 5.22(d, 1H), 5.72~6.02(m, 1H) |
| 4 | —CH$_2$— | —S—[N=N, CH$_3$ thiadiazole] | 4-hydroxyphenyl (p-OH) | H | 80.3 | 128~135 (decomposed) | 2.68(s, 3H), 3.72(s, 2H), 4.41(m, 2H), 4.83(broad s, 2H), 5.23(d, 1H), 5.70~6.03(m, 1H), 6.88(d, 2H), 7.18(s, 1H), 7.53(d, 2H), 8.12(d, 1H) |
| 5 | —CH$_2$— | —S—[N=N, CH$_3$ thiadiazole] | 2,3-dihydroxyphenyl | H | 90.9 | 177~182 (decomposed) | 2.68(s, 3H), 3.70(broad s, 2H), 4.38(m, 2H), 4.78(broad s, 2H), 5.20(d, 1H), 5.68~6.02(m, 1H), 6.62~7.32(m, 4H), 8.45(d, 1H) |
| 6 | —CH$_2$— | —S—[N=N, CH$_3$ thiadiazole] | 3,5-dihydroxyphenyl | H | 84.2 | 125~128 (decomposed) | 2.68(s, 3H), 3.71(broad s, 2H), 4.38(m, 2H), 4.79(broad s, 2H), 5.20(d, 1H), 5.66~6.00(m, 1H), 6.60~7.40(m, 3H), 8.50(m, 1H) |
| 7 | —CH$_2$— | —S—[N=N, CH$_3$ thiadiazole] | 2,5-dihydroxyphenyl | H | 78.6 | 125~130 (decomposed) | 2.69(s, 3H), 3.71(s, 2H), 4.40(m, 2H), 4.85(s, 2H), 5.21(d, 1H), 5.68~6.03(m, 1H), 6.75~7.20(m, 4H), 8.45(d, 1H) |

TABLE 3-continued

Structure:
$H_2N-C(=N)-S-$ attached via $-C(=N-O-B-CONHN=C(Q_1)(Q_2))-CONH-$ to β-lactam with $-CH_2-Z$ and $COOH$

| Example | B | Z | Q₁ | Q₂ | Yield (%) | Melting point (°C.) | ¹H NMR (d₆-DMSO)δ |
|---|---|---|---|---|---|---|---|
| 8(I) | —CH₃— | N=C(CH₃)-S-S- (thiadiazole) | 3,4-dihydroxyphenyl | H | 91.8 | 129~132 (decomposed) | 2.69(s, 3H), 3.74(s, 2H), 4.42(m, 2H), 4.80(broad s, 2H), 5.25 (d, 1H), 5.68~6.06(m, 1H), 6.85~7.46(m, 4H), 8.13(d, 1H) |
| 9 | —CH₃— | N=C(CH₃)-S-S- | 4-chloro-2-hydroxyphenyl | H | 73.0 | 148~157 (decomposed) | 2.70(s, 3H), 3.74(s, 2H), 4.41(m, 2H), 4.87(broad s, 2H), 5.27 (d, 1H), 5.70~6.05(m, 1H), 6.80~7.73(m, 4H), 8.47(d, 1H) |
| 10 | —CH₃— | N=C(CH₃)-S-S- | 4-nitro-2-hydroxyphenyl | H | 84.3 | 173~177 (decomposed) | 2.69(s, 3H), 3.68(broad s, 2H), 4.45(m, 2H), 4.87(broad s, 2H), 5.23 (d, 1H), 5.70~6.05(m, 1H), 6.96~7.54(m, 4H), 8.47(m, 1H) |
| 11 | —CH₃— | N=C(CH₃)-S-S- | 4-methoxy-2-hydroxyphenyl | H | 73.4 | 105~110 (decomposed) | 2.69(s, 3H), 3.71(s, 5H), 4.48(m, 2H), 4.87(broad s, 2H), 5.21 (d, 1H), 5.70~5.98(m, 1H), 6.82~7.25(m, 4H), 8.53(d, 1H) |
| 12 | —CH₃— | N=C(CH₃)-S-S- | 2-hydroxyphenyl | CH₃ | 75.0 | — | 2.47(s, 3H), 2.70(s, 3H), 3.72(s, 2H), 4.40(m, 2H), 4.85(broad s, 2H), 5.22(d, 1H), 5.68~5.98(m, 1H), 6.75~7.84(m, 5H) |

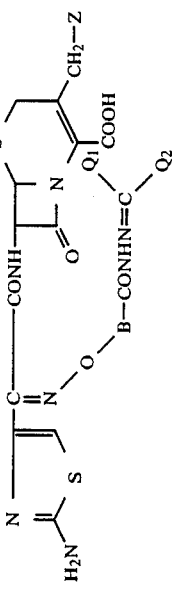

TABLE 3-continued

Structure:

$$\underset{H_2N}{\overset{N}{\underset{S}{\bigvee}}}-C(=N-O-B-CONHN=C\underset{Q_2}{\overset{Q_1}{\diagdown}})-CONH-\text{[β-lactam]}-CH_2-Z$$

with COOH on the cephem ring.

| Example | B | Z | Q₁ | Q₂ | Yield (%) | Melting point (°C) | ¹H NMR (d₆-DMSO)δ |
|---------|-----|-----|-----|-----|-----------|---------------------|---------------------|
| 18 | —CH₂— | -S-[thiadiazole]-CH₃ | 2-hydroxy-phenyl (o-OH) | CH₃ | 94 | 103~107 (decomposed) | 2.45(s, 3H), 3.74(s, 2H), 4.43(m, 2H), 4.86(broad s, 2H), 5.25 (d, 1H), 5.70~6.00(m, 1H), 6.77~7.82(m, 5H), 9.58(s, 1H) |
| 19 | —CH₂— | -S-[thiadiazole]-CH₃ | 3-hydroxy-phenyl (m-OH) | CH₃ | 94 | 105~108 (decomposed) | 2.26(s, 3H), 3.73(broad s, 2H), 4.37(m, 2H), 4.82(broad s, 2H), 5.23 (d, 1H), 5.72~6.00(m, 5H), 6.87~7.49(m, 5H), 9.54(s, 1H) |
| 20 | —CH₂— | -S-[thiadiazole]-CH₃ | 4-hydroxy-phenyl (p-OH) | CH₃ | 91.8 | — | 2.25(s, 3H), 3.72(broad s, 2H), 4.44(m, 2H), 4.88(broad s, 2H), 5.24 (d, 1H), 5.70~6.04(m, 1H), 6.60~7.94(m, 5H), 9.54(s, 1H) |
| 21 | —CH₂— | -S-[thiadiazole]-CH₃ | 3,4-dihydroxy-phenyl | CH₃ | 98.8 | — | 2.30(s, 3H), 3.72(broad s, 2H), 4.37(m, 2H), 4.84(broad s, 2H), 5.23 (d, 1H), 5.68~6.00(m, 1H), 6.75~7.40(m, 4H), 9.56(s, 1H) |
| 22 | —CH₂— | -S-[thiadiazole]-CH₃ | 2,3,4-trihydroxy-phenyl | CH₃ | 90.1 | 109-113 (decomposed) | 2.37(s, 3H), 3.73(broad s, 2H), 4.43(m, 2H), 4.94(broad s, 2H), 5.20 (d, 1H), 5.70~6.03(m, 1H), 6.27~7.55(m, 3H), 9.52(s, 1H) |

TABLE 3-continued

Structure:
$$H_2N-C(=N)-S-\overset{\|}{C}=N-O-B-CONHN=C(Q_1)(Q_2) \text{ linked to } \beta\text{-lactam-CH}_2-Z \text{ with COOH}$$

| Example | B | Z | $Q_1$ | $Q_2$ | Yield (%) | Melting point (°C.) | 1H NMR (d6-DMSO)δ |
|---|---|---|---|---|---|---|---|
| 23 | —CH(CH₃)— | thiadiazole-S- (N=N, S, CH₃) | 4-methyl-2,3-dihydroxyphenyl | H | 84.2 | — | 1.56(d, 3H), 3.75(broad s, 2H), 4.50(m, 2H), 4.90(q, 1H), 5.26(d, 1H), 5.75~6.05(m, 1H), 6.90~7.50(m, 4H), 8.18(d, 1H), 9.68(s, 1H) |
| 24 | —CH(CH₃)— | thiadiazole-S- | 3,4-dihydroxyphenyl | H | 94.2 | 173~179 (decomposed) | 1.54(d, 3H), 3.70(broad s, 2H), 4.42(m, 2H), 4.86(m, 1H), 5.20(d, 1H), 5.65~6.00(m, 1H), 6.30~7.50(m, 3H), 8.45(s, 1H), 9.52(s, 1H) |
| 25(1) | —C(CH₃)₂— | thiadiazole-S- | 3,4-dihydroxyphenyl | H | 90.5 | — (decomposed) | 1.55(s, 6H), 3.72(broad s, 2H), 4.42(m, 2H), 5.22(d, 1H), 5.72~6.13 (m, 1H), 6.73~7.55(m, 4H), 8.20(m, 1H), 9.55(s, 1H) |
| 26(1) | —CH₂— | N-methyl-thiadiazole-S- | 4-methyl-2,3-dihydroxyphenyl | CH₃ | 85.6 | — | 2.35(s, 3H), 3.65(broad s, 2H), 3.92(s, 3H), 4.40(m, 2H), 4.88(broad, s, 2H), 5.10(d, 1H), 5.53~5.98(m, 1H), 6.28~7.48(m, 3H) |
| 27(1) | —CH₂— | H | 4-methyl-2,3-dihydroxyphenyl | H | 96.6 | 192~195 (decomposed) | 2.05(s, 3H), 3.47(broad s, 2H), 4.81(broad s, 2H), 5.19(d, 1H), 5.60~5.93(m, 1H), 6.67~7.45(m, 4H) |

TABLE 3-continued

Structure:

$$\text{H}_2\text{N-C(=N)-S-CH=C(-S-)-CONH-[β-lactam]-CH}_2\text{-S-C(=N-O-B-CONHN=C(Q}_1\text{)(Q}_2\text{))}$$

with CH$_2$-Z group and COOH on the cephem nucleus.

| Example | B | Z | Q$_1$ | Q$_2$ | Yield (%) | Melting point (°C.) | $^1$H NMR (d$_6$-DMSO)δ |
|---|---|---|---|---|---|---|---|
| 28 | —CH$_2$— | $\begin{array}{c}N=N\\ \|\quad\|\\ -S\quad N-CH_3\end{array}$ | 2,3-dihydroxy-methylphenyl (OH, OH, with CH$_3$) | H | 55.6 | — | 3.74(broad s, 2H), 4.02(s, 3H), 4.43(broad s, 2H), 4.92(broad s, 2H), 5.36(d, 1H), 5.79–6.14(m, 1H), 6.86–7.38(m, 4H) |
| 29 | —CH$_2$— | $\begin{array}{c}N=N\\ \|\quad\|\\ -S\quad N-CH_3\end{array}$ | 2,4-dihydroxy-methylphenyl | H | 59.4 | — | 3.74(broad s, 2H), 4.01(s, 3H), 4.42(broad s, 2H), 4.93(broad s, 2H), 5.31(d, 1H), 5.82–6.13(m, 1H), 6.53–7.54(m, 4H) |
| 30 | —CH$_2$— | $\begin{array}{c}N=N\\ \|\quad\|\\ -S\quad N-CH_3\end{array}$ | 2,3-dihydroxy-methylphenyl | CH$_3$ | 61.3 | — | 2.28(s, 3H), 3.66(m, 2H), 4.02(s, 3H), 4.48(m, 2H), 4.99(m, 2H), 5.28(d, 1H), 5.72–6.14(m, 1H), 6.98–7.78(m, 4H) |
| 31 | —CH$_2$— | $\begin{array}{c}N=N\\ \|\quad\|\\ -S\quad N-CH_3\end{array}$ | 3-methoxy-2-hydroxy-methylphenyl (OCH$_3$, OH) | H | 65.3 | — | 3.82(broad s, 2H), 3.88(s, 3H), 4.04(s, 3H), 4.42(broad s, 2H), 4.90(broad s, 2H), 5.24(d, 1H), 5.73–6.14(m, 1H), 6.63–7.42(m, 3H) |
| 32 | —CH—CH$_3$ | $\begin{array}{c}N=N\\ \|\quad\|\\ -S\quad N-CH_3\end{array}$ | 2-methoxy-3,5-dihydroxy-methylphenyl (OCH$_3$, OH, OH) | H | 93.0 | — | 1.55(d, 3H), 3.81(broad s, 2H), 3.92(s, 3H), 4.08(s, 3H), 4.45(broad s, 2H), 5.01(m, 1H), 5.32(d, 1H), 5.74–6.18(m, 1H), 7.08–7.69(m, 3H) |

TABLE 3-continued

[Structure shown: cephalosporin derivative with aminothiazole oxime group connected via O-B-CONHN=C(Q1)(Q2), and CH2-Z substituent]

| Example | B | Z | Q1 | Q2 | Yield (%) | Melting point (°C.) | $^1$H NMR (d$_6$-DMSO)δ |
|---|---|---|---|---|---|---|---|
| 33 | $-\underset{CH_3}{\underset{|}{\overset{CH_3}{\overset{|}{C}}}}-$ | [N-methyltetrazolylthio group] | [2-methoxy-3,4-dihydroxyphenyl] | H | 39.0 | — | 1.63(s, 6H), 3.80(broad s, 2H), 3.91(s, 3H), 4.05(s, 3H), 4.42(broad s, 2H), 5.33(d, 1H), 5.80–6.22(m, 1H), 6.62–7.33(m, 3H) |

Note
(1)These examples were carried out in the same manner as in Example 2.

EXAMPLE 34

Synthesis of sodium 7-{2-[2-amino-1,3-thiazol-4-yl]-2-[1-(3-(3,4-dihydroxybenzylidene)carbazoyl)ethoxyimino]acetamido}-3-[(1,3,4-thiadiazol-2-yl)thiomethyl]-3-cephem-4-carboxylate In 30 ml of water was suspended 0.5 g of 7-{2-[2-amino-1,3-thiazol-4-yl]-2-[1-(3-(3,4-dihydroxybenzylidene)carbozoyl)ethoxyimino]-acetamido}-3-[(1,3,4-thiadiazol-2-yl)thiomethyl]-3-cephem-4-carboxylic acid.hydrochloride obtained in Reference example 23 and the suspension was dissolved at pH about 7.5 by adding an aqueous 5% sodium hydrogencarbonate solution.

After filtration thereof, the filtrate was adsorbed by 100 ml of HP 20 column filled with water and washed with water and 20% methanol-water solution. Then, the title compound was eluted by 50% ethanol-water solution, and after evaporation of methanol and lyophilized to obtain 0.2 g of the title compound.

Structural formula:

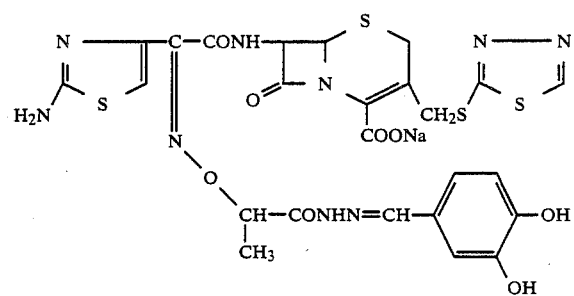

$^1$NMR (d$_6$-DMSO)δ: 1.52 (d, 3H), 3.62 (broad s, 2H), 4.48 (m, 2H), 4.87 (m, 1H), 5.18 (d, 1H), 5.65–5.97 (m, 1H), 6.83–7.52 (m, 4H), 8.18 (s, 1H), 9.60 (s, 1H).

EXAMPLE 35

Synthesis of 7-{2-[2-amino-1,3-thiazol-4-yl]-2-[3-(3,4-diacetoxybenzoyl)carbazoyl]methoxyiminoacetamido}-3-[(5-methyl-1,3,4-thiadiazol-2-yl)thiomethyl]-3-cephem-4-carboxylic acid.hydrochloride In 3 ml of methylene chloride was suspended 0.35 g (0.53 mmole) of 7-[2-(2-amino-1,3-thiazol-4-yl)-2-carbazoylmethoxyiminoacetamido]-3-[(5-methyl-1,3,4-thiadiazol-2-yl)thiomethyl]-3-cephem-4-carboxylic acid.dihydrochloride obtained in Reference example 9 and the suspension was dissolved by adding 1.35 g (6.66 mmole) of N,O-bis(trimethylsilyl)acetamide. To the mixture was added 0.136 g (0.53 mmole) of 3,4-diacetoxybenzoic acid chloride and the mixture was stirred at room temperature for one hour. The mixture was poured into 200 ml of ether and added thereto a small amount of methanol while stirring. The resulting precipitates were collected by filtration, washed with water and then dried to obtain 0.42 g of the title compound. (Yield: 94.1%)

Structural formula:

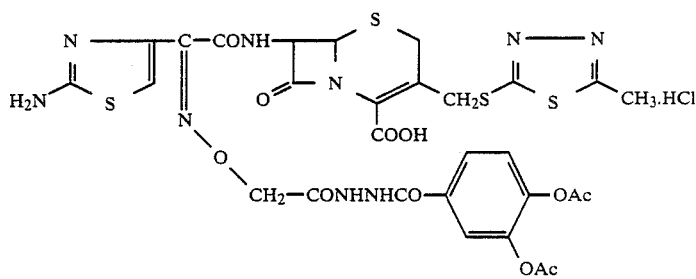

$^1$H NMR (d$_6$-DMSO)δ: 2.32 (s, 6H), 2.68 (s, 3H), 3.72 (broad s, 2H), 4.42 (m, 2H), 4.73 (broad s, 2H), 5.17 (d, 1H), 5.68–6.02 (m, 1H), 6.68–8.08 (m, 4H).

EXAMPLE 36

Synthesis of 7-{2-[2-amino-1,3-thiazol-4-yl]-2-[3-(3,4-diacetoxybenzoyl)carbazoyl]methoxyiminoacetamido}-3-[(1-methyl-1,2,3,4-tetrazol-5-yl)thiomethyl]-3-cephem-4-carboxylic acid.hydrochloride (I) In 5 ml of methylene chloride was suspended 0.566 g (0.7 mmole) of 7-[2-(2-amino-1,3-thiazol-4-yl)-2-carbazoylmethoxyiminoacetamido]-3-[(1-methyl-1,2,3,4-tetrazol-5-yl)thiomethyl]-3-cephem-4-carboxylic acid diphenylmethyl ester.dihydrochloride, and 1.25 g (6.15 mmole) of N,O-bis(trimethylsilyl)acetamido was added thereto to form a solution. To the solution was added 0.2 g (0.78 mmole) of 3,4-diacetoxybenzoic acid chloride and the mixture was stirred at room temperature for one hour. The resulting mixture was poured into 200 ml of ether and a small amount of methanol was added thereto while stirring. Resulting precipitates were collected by filtration, washed with ether and then dried to obtain 0.68 g of the diphenylmethyl ester of the title compound. (Yield: 97.9%)

(II) A mixture comprising 6 ml of trifluoroacetic acid and 1.5 ml of anisole was ice-cooled, 0.68 g (0.685 mmole) of the above diphenylmethyl ester was added thereto and the mixture was stirred for 30 minutes under ice-cooling. The resulting mixture was added dropwise into 150 ml of ether while vigorously stirring and resulting precipitates were collected by filtration, washed with ether and then dried to obtain 0.54 g of the title compound. (Yield: 95.4%)

Structural formula:

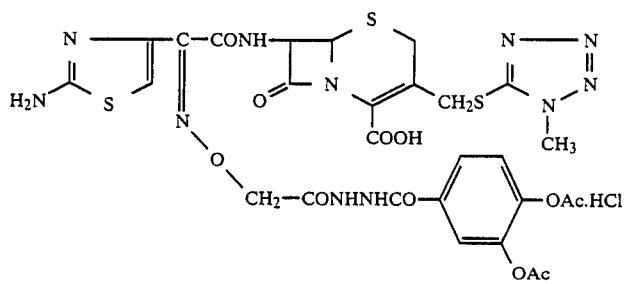

$^1$H NMR (d$_6$-DMSO)δ: 2.32 (s, 6H), 3.70–4.10 (m, 5H), 4.35 (m, 2H), 4.86 (broad s, 2H), 5.52 (d, 1H), 5.65–6.03 (m, 1H), 7.05–8.17 (m, 4H).

EXAMPLES 37 TO 46

In the same manner as in Example 36, hydrochlorides of the β-lactam compounds represented by the following formula were synthesized. The results are shown in Table 4.

TABLE 4

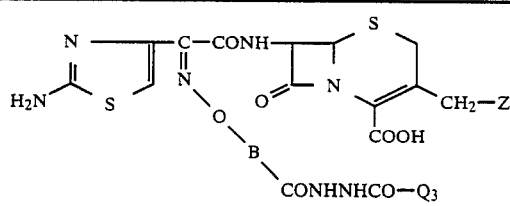

| Example | B | Z | Q$_3$ | Yield (%) | $^1$H NMR(d$_6$-DMSO)δ |
|---|---|---|---|---|---|
| 37 | —CH$_2$— | -S-(thiadiazole) | phenyl-OAc,OAc | 98.3 | 2.32(s, 6H), 3.73(broad s, 2H), 4.46(m, 2H), 4.75(broad s, 2H), 5.20(d, 1H), 5.70~6.05(m, 1H), 6.70~8.10(m, 4H), 9.60(s, 1H) |
| 38 | " | -S-(N-methyl tetrazole) | phenyl-OAc,OAc | 94.6 | 2.28(s, 6H), 3.69~4.03(m, 5H), 4.32(m, 2H), 4.82(broad s, 2H), 5.18(d, 1H), 5.70~5.93(m, 1H), 6.87~7.78(m, 4H) |
| 39 | " | -S-(thiadiazole) | " | 96.6 | 2.30(s, 6H), 3.76(s, 2H), 4.50(m, 2H), 4.83(broad s, 2H), 5.23(d, 1H), 5.70~6.02(m, 1H), 6.86~7.73(m, 4H), 9.56(s, 1H) |
| 40 | " | " | —CH=CH—phenyl-OAc,OAc | 99.5 | 2.33(s, 6H), 3.75(s, 2H), 4.50(m, 2H), 4.85(broad s, 2H), 5.24(d, 1H), 5.68~5.97(m, 1H), 6.80~7.78(m, 4H) |
| 41 | —CH— \| CH$_3$ | " | phenyl-OAc,OAc | 95.0 | 1.46(d, 3H), 2.25(s, 6H), 3.82(broad s, 2H), 4.38(m, 2H), 4.83(q, 1H), 5.27(d, 1H), 5.76~6.20(m, 1H), 6.70~7.43(m, 4H), 9.64(s, 1H) |
| 42 | —CH$_2$— | -S-(N-methyl tetrazole) | phenyl-OAc,OAc,AcO | 43.8 | 2.35(s, 9H), 3.78(broad s, 2H), 4.01(s, 3H), 4.36(m, 2H), 4.84(broad s, 2H), 5.26(d, 1H), 5.74–6.14(m, 1H), 7.28–8.14(m, 3H) |

TABLE 4-continued

[Structure: thiazole-aminothiazole cephem with CONHNHCO-Q3 substituent]

| Example | B | Z | Q3 | Yield (%) | $^1$H NMR(d$_6$-DMSO)δ |
|---|---|---|---|---|---|
| 43 | " | " | -CH=CH-C$_6$H$_2$(AcO)(OAc)(OCH$_3$) | 52.3 | 2.38(s, 6H), 3.81(broad s, 2H), 4.01(broad s, 6H), 4.42(m, 2H), 4.92(broad s, 2H), 5.31(d, 1H), 5.76–6.14(m, 1H), 7.27–8.23(m, 3H) |
| 44 | -CH(CH$_3$)- | " | C$_6$H$_2$(AcO)(OAc)(OCH$_3$) | 54.6 | 1.52(d, 3H), 2.33(s, 6H), 3.81(broad s, 2H), 3.98(s, 3H), 4.01(s, 3H), 4.42(m, 2H), 5.03 (m, 1H), 5.31(d, 1H), 5.83–6.22(m, 1H), 7.22–8.03(m, 3H) |
| 45 | -C(CH$_3$)$_2$- | " | " | 47.3 | 1.53(s, 6H), 2.32(s, 6H), 3.82(broad s, 2H), 3.97(s, 3H), 4.03(s, 3H), 4.41(m, 2H), 5.31(d, 1H), 5.81–6.23(m, 1H), 7.28–8.07(m, 3H) |
| 46 | " | " | C$_6$H$_2$(AcO)(OAc)(OAc)CH$_3$ | 61.3 | 1.54(s, 6H), 2.33(s, 9H), 3.81(broad s, 2H), 4.03(s, 3H), 4.41(m, 2H), 5.33(d, 1H), 5.82–6.20(m, 1H), 7.21–8.13(m, 3H) |

EXAMPLE 47

Synthesis of ammonium 7-{2-[2-amino-1,3-thiazol-4-yl]-2-[3-(3,4-dihydroxybenzoyl)carbazoyl]methoxyiminoacetamido}-3-[(1,3,4-thiadiazol-2-yl)thiomethyl]-3-cephem-4-carboxylate In 10 ml of methanol was dissolved 0.4 g (0.505 mmole) of 7-{2-[2-amino-1,3-thiazol-4-yl]-2-[3-(3,4-diacetoxybenzoyl)carbazoyl]methoxyiminoacetamido}-3-[(1,3,4-thiadiazol-2-yl)thiomethyl]-3-cephem-4-carboxylic acid.hydrochloride obtained in Example 37, and 0.15 ml of 25% aqueous ammonia was added thereto and the mixture was stirred at room temperature for one hour.

To the resulting mixture was added 20 ml of ether and resulting precipitates were collected by filtration, washed with ether and then dried to obtain 0.31 g of the title compound. (Yield: 86.7%)

Structural formula:

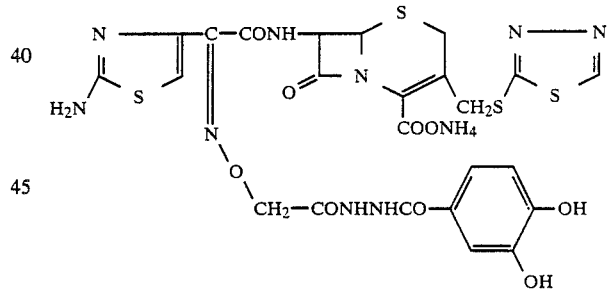

$^1$NMR (d$_6$-DMSO)δ: 3.82 (broad s, 2H), 4.46 (m, 2H), 4.83 (broad s, 2H), 5.30 (d, 1H), 5.80–6.10 (m, 1H), 6.80–8.15 (m, 4H), 9.60 (s, 1H).

EXAMPLE 48

Synthesis of 7-{2-[2-amino-1,3-thiazol-4-yl]-2-[3-((3,4-diacetoxybenzoyl)carbamoyl)carbazoyl]methoxyiminoacetamido}-3-[(5-methyl-1,3,4-thiadiazol-2-yl)thiomethyl]-3-cephem-4-carboxylic acid.hydrochloride In 2 ml of methylene chloride was suspended 0.257 g (0.39 mmole) of 7-{2-[2-amino-1,3-thiazol-4-yl]-2-carbazoylmethoxyiminoacetamido}-3-[(5-methyl-1,3,4-thiadiazol-2-yl)thiomethyl]-3-cephem-4-carboxylic acid.dihydrochloride obtained in Reference example 9, and 1 g of N,O-bis(trimethylsilyl)acetamide was added thereto to form a solution. To the resulting solution was added 0.22 g (0.84 mmole) of 3,4-diacetoxybenzoylisocyanate and the mixture was stirred at room temperature for 8 hours. The resulting mixture was poured into 100 ml of ether and a small amount of methanol was added thereto while stirring. Resulting precipitates were collected by filtration, washed with ether and then dried to obtain 0.33 g of the title compound. (Yield: 84.6%)

Melting point: 73° to 76° C. (decomposed).
Structural formula:

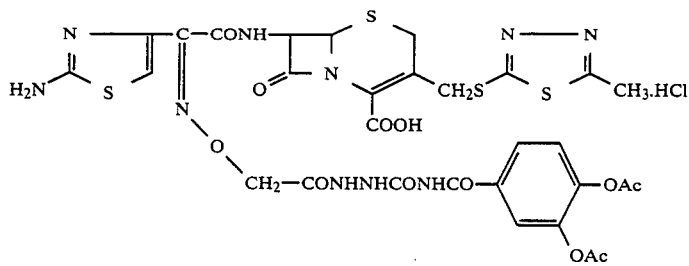

¹H NMR (d₆-DMSO)δ: 2.34 (s, 6H), 2.71 (s, 3H), 3.74 (broad s, 2H), 4.43 (m, 2H), 4.82 (broad s, 2H), 5.22 (d, 1H), 5.68–5.98 (m, 1H), 7.08–8.06 (m, 4H).

EXAMPLE 49

Synthesis of 7-{2-[2-amino-1,3-thiazol-4-yl]-2-[3-((3,4-diacetoxybenzoyl)carbamoyl)carbazoyl]methoxyiminoacetamido}-3-[(1,3,4-thiadiazol-2-yl)thiomethyl]-3-cephem-4-carboxylic acid.hydrochloride In the same manner as in Example 48 except for using 0.387 g (0.6 mmole) of 7-{2-(2-amino-1,3-thiazol-4-yl)-2-carbazoylmethoxyiminoacetamido}-3-[(1,3,4-thiadiazol-2-yl)thiomethyl]-3-cephem-4-carboxylic acid.dihydrochloride obtained in Reference example 10, 4 ml of methylene chloride, 1 g (4.9 mmole) of N,O-bis(-trimethylsilyl)acetamide and 0.332 g (1.26 mmole) of 3,4-diacetoxybenzoylisocyanate, 0.49 g of the title compound was obtained. (Yield: 93.7%)

Structural formula:

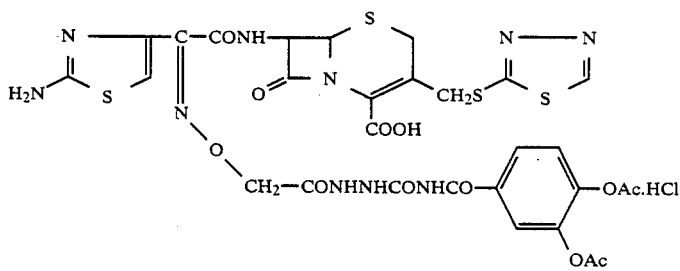

¹H NMR (d₆-DMSO)δ: 2.24 (s, 6H), 3.65 (broad s, 2H), 4.40 (m, 2H), 4.70 (broad s, 2H), 5.12 (d, 1H), 5.58–5.95 (m, 1H), 7.05–8.13 (m, 4H), 9.53 (s, 1H).

EXAMPLE 50

Synthesis of ammonium 7-{2-[2-amino-1,3-thiazol-4-yl]-2-[3-((3,4-dihydroxybenzoyl)carbamoyl)carbazoyl]methoxyiminoacetamido}-3-[(1,3,4-thiadiazol-2-yl)thiomethyl]-3-cephem-4-carboxylate In 10 ml of methanol was dissolved 0.41 g (0.47 mmole) of 7-{2-[2-amino-1,3-thiazol-4-yl]-2-[3-((3,4-diacetoxybenzoyl)carbamoyl)carbazoyl]methoxyiminoacetamido}-3-[(1,3,4-thiadiazol-2-yl)thiomethyl]-3-cephem-4-carboxylic acid hydrochloride obtained in Example 49, and 0.3 ml of 25% aqueous ammonia was added thereto and the mixture was stirred at room temperature for one hour. To the resulting solution was added 0.22 g (0.84 mmole) of 3,4-diacetoxybenzoylisocyanate and the mixture was stirred at room temperature for 8 hours. To the resulting mixture was added 20 ml of ether and resulting precipitates were collected by filtration, washed with ether and then dried to obtain 0.26 g of the title compound. (Yield: 70.3%)

Structural formula:

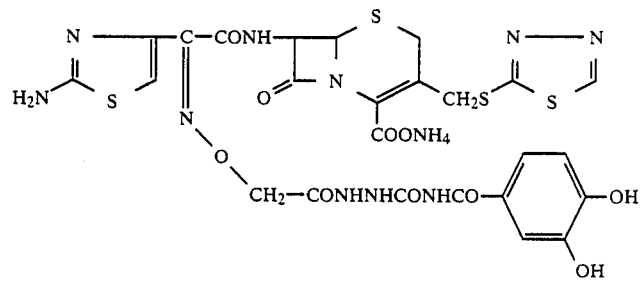

¹H NMR (d₆-DMSO)δ: 3.64 (broad s, 2H), 4.48 (m, 2H), 4.70 (broad s, 2H), 5.12 (d, 1H), 5.60–5.90 (m, 1H), 6.75–7.70 (m, 4H), 9.50 (s, 1H).

EXAMPLE 51

Synthesis of
7-{2-[2-amino-1,3-thiazol-4-yl]-2-[3-((3,5-diacetoxybenzoyl)carbamoyl)carbazoyl]methoxyiminoacetamido}-3-[(1,3,4-thiadiazol-2-yl)thiomethyl]-3-cephem-4-carboxylic acid.hydrochloride (I) In 4 ml of methylene chloride was suspended 0.486 g (0.6 mmole) of 7-[2-(2-amino-1,3-thiazol-4-yl)-2-carbazoylmethoxyiminoacetamido]-3-[(1,3,4-thiadiazol-2-yl)thiomethyl]-3-cephem-4-carboxylic acid diphenylmethyl ester.dihydrochloride, and 1 g (4.9 mmole) of N,O-bis(trimethylsilyl)acetamido was added thereto to form a solution. To the solution was added 0.33 g (1.25 mmole) of 3,5-diacetoxybenzoylisocyanate and the mixture was stirred at room temperature for two hours. The resulting mixture was poured into 150 ml of ether and a small amount of methanol was added thereto while stirring. Resulting precipitates were collected by filtration, washed with ether and then dried to obtain 0.59 g of the diphenylmethyl ester of the title compound. (Yield: 94.8%)

(II) A mixture comprising 6 ml of trifluoroacetic acid and 1.5 ml of anisole was ice-cooled, 0.59 g of the above diphenylmethyl ester was added thereto and the mixture was stirred for 30 minutes under ice-cooling. The resulting mixture was added dropwise into 150 ml of ether while vigorously stirring and resulting precipitates were collected by filtration, washed with ether and then dried to obtain 0.48 g of the title compound. (Yield: 96.6%)

Structural formula:

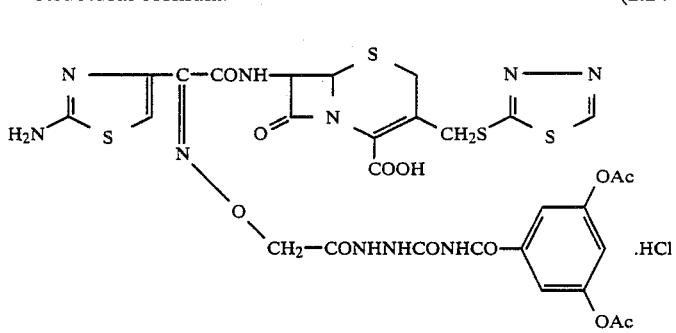

$^1$H NMR (d$_6$-DMSO)δ: 2.30 (s, 6H), 3.74 (broad s, 2H), 4.50 (m, 2H), 4.80 (broad s, 2H), 5.20 (d, 1H), 5.63–6.00 (m, 1H), 6.98–7.92 (m, 4H), 9.56 (s, 1H).

REFERENCE EXAMPLE 12

Synthesis of
2-(2-amino-1,3-thiazol-4-yl)-2-[3-(3,4-dihydroxybenzylidene)carbazoyl]methoxyiminoacetic acid.hydrochloride In 50 ml of ice-cooled methanol was added 5.21 g (34 mmole) of phosphorus oxychloride, and then to the mixture was added 5.4 g (17.1 mmole) of 2-(2-formylamino-1,3-thiadiazol-4-yl)-2-(3-formylcarbazoyl)-methoxyiminoacetic acid and the mixture was stirred for one hour under ice-cooling. The resulting mixture was added dropwise into 400 ml of ether while vigorously stirring and resulting precipitates were collected by filtration, washed with ether and then dried to obtain 4.28 g of 2-(2-amino-1,3-thiadiazol-4-yl)-2-carbazoylmethoxyiminoacetic acid.dihydrochloride. (Yield: 75.4%)

$^1$H NMR (d$_6$-DMSO+D$_2$O)δ: 4.82 (s, 2H), 7.14 (s, 1H).

In 40 ml of methanol was dissolved 2.325 g (7 mmole) of the above dihydrochloride, and 0.967 g (7 mmole) of 3,4-dihyroxybenzaldehyde was added thereto and the mixture was stirred at room temperature for one hour.

The resulting mixture was added dropwise into 400 ml of ether while vigorously stirring and resulting precipitates were collected by filtration, washed with ether and then dried to obtain 2.20 g of the title compound. (Yield: 75.6%)

Structural formula:

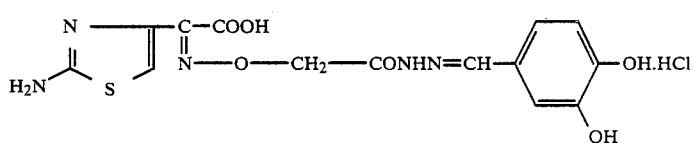

$^1$H NMR (d$_6$-DMSO+D$_2$O)δ: 4.82 (s, 2H), 6.85–7.15 (m, 4H), 7.88–8.22 (d, 1H).

EXAMPLE 52

Synthesis of
7-{2-[2-amino-1,3-thiazol-4-yl]-2-[3-(3,4-dihydroxybenzylidene)carbazoyl]methoxyiminoacetamido}-3-[(1,3,4-thiadiazol-2-yl)thiomethyl]-3-cephem-4-carboxylic acid hydrochloride In 10 ml of DMF were dissolved 0.93 g (2.24 mmole) of 2-(2-amino-1,3-thiazol-4-yl)-2-[3-(3,4-dihydroxybenzylidene)carbazoyl]methoxyiminoacetic acid.hydrochloride obtained in Reference example 12 and 1.11 g (2.24 mmole) of 7-amino-3-[(1,3,4-thiadiazol-2-yl)-thiomethyl]-3-cephem-4-carboxylic acid diphenylmethyl ester and the mixture was ice-cooled, and 0.598 g (2.9 mmole) of DCC was added thereto and stirred at room temperature for one hour. After filtration of the resulting mixture, to the filtrate was added the same amount of chloroform and the mixture was added dropwise into 400 ml of ether while vigorously stirring. Resulting precipitates were collected by filtration, washed with ether and then dried to obtain 2.36 g of the crude product. This product was purified through column chromatography [30 g of silica gel, eluent: chloroform-methanol-formic acid (3:1:1)] to obtain 1.13 g (Yield: 56.4%) of aimed diphenylmethyl ester compound. A mixture comprising 8 ml of trifluoroacetic acid and 2 ml of anisole was ice-cooled, and to the mixture was added 1.13 g (1.26 mmole) of the diphenylmethyl ester obtained above and the mixture was stirred for 30 minutes. The resulting mixture was added dropwise into 150 ml of ether while vigorously stirring and resulting precipitates were collected by filtration, washed with ether and then dried to obtain 0.89 g of the title compound as pale yellow powder. (Yield: 97.0% Physical properties thereof are accorded with those of the compound of Example 16.

REFERENCE EXAMPLE 13

Synthesis of 2-(2-amino-1,3-thiazol-4-yl)-2-[3-(3,4-dihydroxybenzoyl)carbazoyl]methoxyiminoacetic acid.hydrochloride In 50 ml of methylene chloride was suspended 6.12 g (19.4 mmole) of 2-(2-amino-1,3-thiazol-4-yl)-2-carbazoylmethoxyiminoacetic acid tert-butyl ester, and to the suspension was added 20.8 g (102.3 mmole) of N,O-bis(trimethylsilyl)acetamide to form a solution. To the ice-cooled solution was added 5.467 g (21.3 mmole) of 3,4-diacetoxybenzoic acid chloride and the mixture was stirred for 2 hours under ice-cooling. The resulting mixture was poured into 800 ml of ether and to the mixture was added a small amount of methanol while stirring. Resulting precipitates were collected by filtration, washed with ether and then dried to obtain 10.2 g of 2-(2-amino-1,3-thiazol-4-yl)-2-[3-(3,4-diacetoxybenzoyl)carbazoyl]methoxyiminoacetic acid tert-butyl ester hydrochloride. (Yield: 98.2%)

$^1$H NMR (d$_6$-DMSO+D$_2$O)δ: 1.54 (s, 9H), 2.28 (s, 6H), 4.82 (s, 2H), 7.10-8.00 (m, 4H).

In 100 ml of methanol was dissolved 5.69 g (10.6 mmole) of the above hydrochloride, then 4.2 ml of 25% aqueous ammonia was added thereto and the mixture was stirred at room temperature for one hour. The resulting mixture was concentrated, and the residue was dissolved in 200 ml of 30% THF-ethyl acetate, dried over anhydrous magnesium sulfate and then the solvent was distilled out after filtration. The resulting oily product was dissolved in 20 ml of trifluoroacetic acid and the solution was stirred at room temperature for 5 hours. Then, the resulting mixture was added dropwise into 400 ml of ether while vigorously stirring and resulting precipitates were collected by filtration, washed with ether and then dried to obtain 3.9 g of trifluoroacetic acid salt of the title compound. To 20 ml of ice-cooled methanol was added 3.1 g (20 mmole) of phosphorus oxychloride, and 3.9 g of the previously obtained trifluoroacetic acid salt was added thereto and the mixture was stirred for 10 minutes. The resulting mixture was added dropwise into 400 ml of ether while vigorously stirring and resulting precipitates were collected by filtration, washed with ether and then dried to obtain 3.4 g of the title compound. (Yield: 74.3%)

Melting point: 157° to 159° C. (decomposed).

Structural formula:

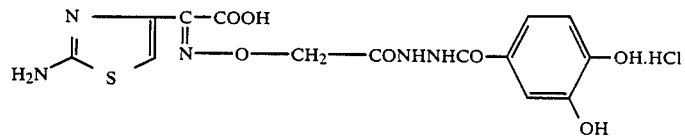

$^1$H NMR (d$_6$-DMSO+D$_2$O) δ: 4.82 (s, 2H), 7.12-7.98 (m, 4H).

REFERENCE EXAMPLES 14 TO 22

In the same manner as in Reference example 13, hydrochlorides of the compounds represented by the following formula were prepared. The results are shown in Table 5.

TABLE 5

| Reference example | B | Q$_3$ | Yield (%) | $^1$H NMR(d$_6$-DMSO) |
|---|---|---|---|---|
| 14 | —CH$_2$— | —C$_6$H$_4$—OH | 74.7 | 4.84(s, 2H), 6.90(d, 2H), 7.18(s, 1H), 7.79(d, 2H) |
| 15 | " | 3,4-(OH)$_2$—C$_6$H$_3$— (with additional OH) | 92.3 | 4.82(s, 2H), 6.95(s, 2H), 7.20(s, 1H) |
| 16 | —CH(CH$_3$)— | —C$_6$H$_4$—OH | 8.23 | 1.54(d, 3H), 4.89(q, 1H), 6.96(d, 2H), 7.25(s, 1H), 7.87(d, 2H) |

TABLE 5-continued $$\underset{H_2N}{\overset{N}{\diagdown}}\underset{S}{\overset{}{\diagup}}\overset{C-COOH}{\underset{N-O-B-CONHNHCO-Q_3}{\|}}$$

| Reference example | B | Q₃ | Yield (%) | ¹H NMR(d₆-DMSO) |
|---|---|---|---|---|
| 17 | —CH₂— | 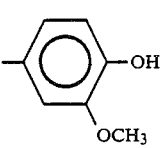 | 87.5 | 3.91(s, 3H), 4.88(s, 2H), 6.97–7.83(m, 4H) |
| 18 | " | 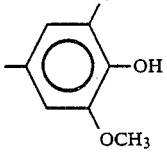 | 79.0 | 3.88(s, 3H), 4.90(s, 2H), 7.23–7.42(m, 3H) |
| 19 | " | 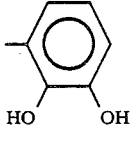 | 68.5 | 4.91(s, 2H), 6.83–7.62(m, 3H), 7.21(s, 1H) |
| 20 | —CH—<br>\|<br>CH₃ | 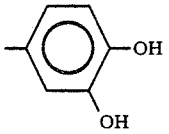 | 84.5 | 1.54(d, 3H), 4.92(q, 1H), 6.78–7.63(m, 4H) |
| 21 | CH₃<br>\|<br>—C—<br>\|<br>CH₃ | " | 87.8 | 1.63(s, 6H), 6.87–7.65(m, 4H) |
| 22 | " | 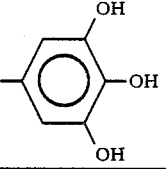 | 73.5 | 1.64(s, 6H), 7.12(s, 2H), 7.41(s, 1H) |

EXAMPLE 53

Synthesis of 7-{2-[2-amino-1,3-thiazol-4-yl]-2-[3-(3,4-dihydroxybenzoyl)carbazoyl]methoxyiminoacetamido}-3-[(1,3,4-thiadiazol-2-yl)thiomethyl]-3-cephem-4-carboxylic acid.hydrochloride (I) In 10 ml of DMF were dissolved 1.295 g (3 mmole) of 2-(2-amino-1,3-thiazol-4-yl)-2-[3-(3,4-dihydroxybenzoyl)carbazoyl]methoxyiminoacetic acid.hydrochloride obtained in Reference example 13 and 1.49 g (3 mmole) of 7-amino-3-[(1,3,4-thiadiazol-2-yl)-thiomethyl]-3-cephem-4-carboxylic acid diphenylmethyl ester and the mixture was ice-cooled, and 0.825 g (4 mmole) of DCC was added therto and stirred at room temperature for one hour. After filtration of the resulting mixture, to the filtrate was added the same amount of chloroform and the mixture was added dropwise into 400 ml of ether while vigorously stirring. Resulting precipitates were collected by filtration, washed with ether and then dried to obtain 2.68 g of the diphenylmethyl ester of the title compound. (Yield: 98.1%)

(II) A mixture comprising 4 ml of trifluoroacetic acid and 1 ml of anisole was ice-cooled, and to the mixture was added 0.3 g (0.33 mmole) of the diphenylmethyl ester obtained above and the mixture was stirred for 30 minutes. The resulting mixture was added dropwise into 80 ml of ether while vigorously stirring and resulting precipitates were collected by filtration, washed with ether and then dried to obtain 0.24 g of the title compound. (Yield: 97.7%) Physical properties thereof are accorded with those of the compound obtained in Example 47.

EXAMPLES 54 TO 84

In the same manner as in Example 53, hydrochlorides of the β-lactam compounds represented by the formula shown below were prepared. The results are shown in Table 6.

TABLE 6

Structure:

H₂N—C(=N)—S—[thiazole]—C(=N—O—B(CONHNHCO—Q₃))—CONH—[β-lactam]—CH₂—Z with COOH

| Example | B | Z | Q₃ | Yield (%) | ¹H NMR (d₆-DMSO) |
|---------|---|---|-----|-----------|------------------|
| 54 | —CH₂— | 1,3,4-thiadiazol-2-ylthio, 5-CH₃ (N=N, S, S, CH₃) | 4-hydroxyphenyl | 80.6 | 2.68(s, 3H), 3.62(m, 2H), 4.50(m, 2H), 4.71(m, 2H), 5.08(d, 1H), 5.54~5.88(m, 1H), 6.93(d, 2H), 7.87(d, 2H) |
| 55 | —CH₂— | 1-methyl-tetrazol-5-ylthio | 2-hydroxyphenyl | 71.5 | 3.63(broad s, 2H), 3.90(s, 3H), 4.40(m, 2H), 4.80(broad s, 2H), 5.12(d, 1H), 5.55~5.99(m, 1H), 6.75~8.15(m, 5H) |
| 56 | —CH₂— | —OOCCH₃ | 3,4-dihydroxyphenyl | 90.0 | 2.00(s, 3H), 3.52(broad s, 2H), 4.73(broad s, 2H), 5.10(d, 1H), 5.52~5.81(m, 1H), 6.79~7.53(m, 4H) |
| 57 | —CH₂— | —OOCNH₂ | 3,4-dihydroxyphenyl | 59.9 | 3.73(broad s, 2H), 4.70(broad s, 2H), 5.08(d, 1H), 5.50~5.83(m, 1H), 6.58~7.46(m, 4H) |
| 58 | —CH₂— | 1H-1,2,3-triazol-5-ylthio | 3,4-dihydroxyphenyl | 61.2 | 3.80(broad s, 2H), 4.44(m, 2H), 4.80(broad s, 2H), 5.20(d, 1H), 5.52~5.98(m, 1H), 6.75~8.12(m, 5H) |
| 59 | —CH₂— | 5-methyl-1,3,4-thiadiazol-2-ylthio | 3,4-dihydroxyphenyl | 79.9 | 2.65(s, 3H), 3.63(broad s, 2H), 4.48(m, 2H), 4.73(broad s, 2H), 5.08(d, 1H), 5.62~5.88(m, 1H), 6.72~7.43(m, 4H) |
| 60 | —CH₂— | 6-hydroxy-3-methyl-5-oxo-1,2,4-triazin-3-ylthio (N—N, S, OH, N—CH₃, O) | 3,4-dihydroxyphenyl | 77.6 | 3.25(s, 3H), 3.58(broad s, 2H), 4.26(m, 2H), 4.78(broad s, 2H), 5.04(d, 1H), 5.53~5.84(m, 1H), 6.68~7.54(m, 4H) |
| 61 | —CH₂— | 1-methyl-6-hydroxy-5-oxo-1,2,4-triazin-3-ylthio | 3,4-dihydroxyphenyl | 36.5 | 3.58~3.78(m, 5H), 4.31(m, 2H), 4.66(broad s, 2H), 5.07(d, 1H), 5.51~5.91(m, 1H), 6.74~7.60(m, 4H) |
| 62 | —CH₂— | 1-methyl-1,2,3,4-tetrazol-5-ylthio | 3,4-dihydroxyphenyl | 70.6 | 3.72(broad s, 2H), 3.92(s, 3H), 4.33(m, 2H), 4.68(broad s, 2H), 5.06(d, 1H), 5.53~5.88(m, 1H), 6.75~7.58(m, 4H) |

TABLE 6-continued

Structure:
```
       N  ╱═╲  C—CONH— [β-lactam with S]
H2N—⟨  ⟩                       CH2—Z
       S   N                   
           ‖                   
           N                   COOH
            \                  
             O                 
              \                
               B—CONHNHCO—Q3
```

| Example | B | Z | Q3 | Yield (%) | ¹H NMR (d6-DMSO) |
|---|---|---|---|---|---|
| 63 | —CH2— | tetrazole-S with N-CH2-COOH | phenyl-3,4-diOH | 84.2 | 3.70(s, 2H), 4.17~4.48(m, 2H), 4.70(s, 2H), 5.11(d, 1H), 5.28(s, 2H), 5.52~5.96(m, 1H), 6.98~7.55(m, 4H) |
| 64 | —CH2— | tetrazole-S with N-CH2-SO3H | phenyl-OH | 63.0 | 3.68(broad s, 2H), 4.30(m, 2H), 4.62(broad s, 2H), 5.02(d, 1H), 5.26(broad s, 2H), 5.48~5.90(m, 1H), 6.70~7.44(m, 4H) |
| 65 | —CH2— | tetrazole-S with N-CH2-CH2-OH | phenyl-OH | 83.3 | 3.50~4.02(m, 3H), 4.25~4.83(m, 6H), 5.18(d, 1H), 5.63~5.98(m, 1H), 6.83~7.63(m, 3H) |
| 66 | —CH2— | tetrazole-S with N-CH2-CH=CH2 | phenyl-OH | 69.7 | 3.70(broad s, 2H), 4.20~4.87(m, 6H), 5.18~6.22(m, 5H), 6.68~7.43(m, 4H) |
| 67 | —CH2— | tetrazole-S with N-CH2-CH2-N(CH3)2 | phenyl-OH | 22.5 | 2.24(s, 6H), 2.68(m, 2H), 3.70(broad s, 2H), 4.18~4.38(m, 4H), 4.64(broad s, 2H), 5.08(d, 1H), 5.60~5.92(m, 1H), 6.78~7.62(m, 4H) |
| 68 | —CH2— | thiadiazole-S with CH3 | phenyl-2,3,4-triOH | 45.0 | 2.68(s, 3H), 3.72(broad s, 2H), 4.42(m, 2H), 4.78(broad s, 2H), 5.19(d, 1H), 5.68~6.03(m, 1H), 6.91~7.28(m, 3H) |
| 69 | —CH—<br>CH3 | thiadiazole-S with CH3 | phenyl-OH | 77.3 | 1.52(d, 3H), 3.60(m, 2H), 4.47(m, 2H), 4.78(m, 1H), 5.05(d, 1H), 5.53~5.88(m, 1H), 6.92(d, 2H), 6.99(s, 1H), 7.84(d, 2H) |
| 70 | —CH—<br>CH3 | —OOCCH3 | phenyl-3,4-diOH | 73.3 | 1.43(d, 3H), 2.01(s, 3H), 3.53(broad s, 2H), 4.76(broad s, 2H), 4.90(q, 1H), 5.08(d, 1H), 5.55~5.88(m, 1H), 6.73~7.48(m, 4H) |
| 71 | —CH2— | tetrazole-S with N-CH3 | phenyl-3-OH, 4-OCH3 | 59.1 | 3.69(broad s, 2H), 3.87(s, 3H), 3.96(s, 3H), 4.38(m, 2H), 4.81(broad s, 2H), 5.08(d, 1H), 5.54-5.92(m, 1H), 6.84-7.62(m, 4H) |

TABLE 6-continued
| Example | B | Z | Q₃ | Yield (%) | ¹H NMR (d₆-DMSO) |
|---|---|---|---|---|---|
| 72 | —CH₂— | 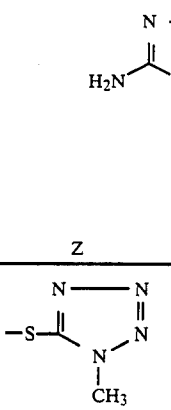 | 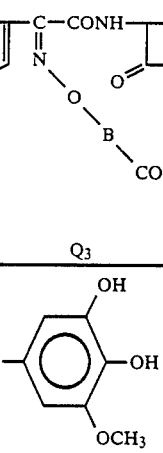 | 55.9 | 3.72(broad s, 2H), 3.88(s, 3H), 3.99(s, 3H), 4.41(m, 2H), 4.87(broad s, 2H), 5.28(d, 1H), 5.82–6.13(m, 1H), 7.17–7.33(m, 3H) |
| 73 | —CH₂— | 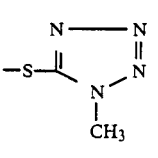 | 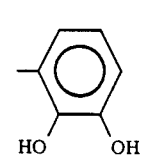 | 54.1 | 3.78(broad s, 2H), 3.98(s, 3H), 4.47(m, 2H), 4.88(broad s, 2H), 5.29(d, 1H), 5.80–6.17(m, 1H), 6.92–7.71(m, 4H) |
| 74 | —CH₂— | 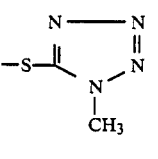 | 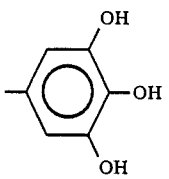 | 34.7 | 3.76(broad s, 2H), 3.99(s, 3H), 4.45(m, 2H), 4.89(broad s, 2H), 5.23(d, 1H), 5.72–6.12(m, 1H), 6.89–7.32(m, 3H) |
| 75 | 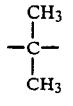 | 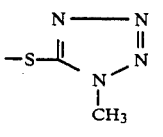 | 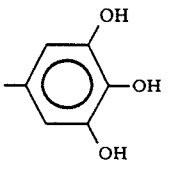 | 53.7 | 1.53(s, 6H), 3.78(broad s, 2H), 4.01(s, 3H), 4.48(m, 2H), 5.24(d, 1H), 5.74–6.18(m, 1H), 7.28(s, 3H) |
| 76 | 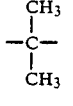 | 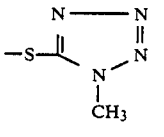 | 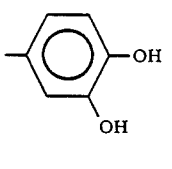 | 59.4 | 1.52(s, 6H), 3.76(m, 2H), 4.02(s, 3H), 4.62(m, 2H), 5.22(d, 1H), 5.72–6.09(m, 1H), 6.89–7.72(m, 4H) |
| 77 | 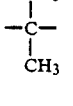 | 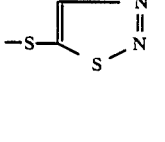 | 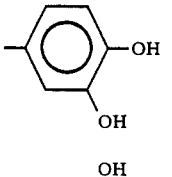 | 57.3 | 1.52(s, 6H), 3.77(m, 2H), 4.58(m, 2H), 5.23(d, 1H), 5.70–6.12(m, 1H), 6.88–7.69(m, 4H), 8.97(s, 1H) |
| 78 | 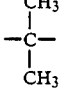 | 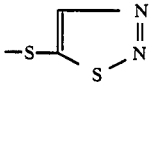 | 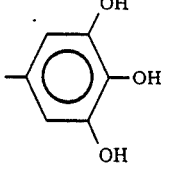 | 52.8 | 1.52(s, 6H), 3.76(m, 2H), 4.59(m, 2H), 5.22(d, 1H), 5.78–6.14(m, 1H), 6.93–7.30(m, 3H), 8.99(s, 1H) |
| 79 | —CH₂— | 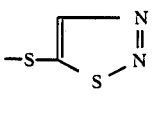 | 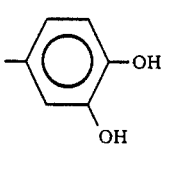 | 59.6 | 3.70(broad s, 2H), 4.41(m, 2H), 4.67(broad s, 2H), 5.16(d, 1H), 5.80–6.18(m, 1H), 6.97–7.76(m, 4H), 8.97(s, 1H) |

TABLE 6-continued

Structure (common to all examples):

Thiazolyl-C(=N-O-B-CONHNHCO-Q₃)-CONH- attached to β-lactam-S ring with =CH-CH₂-Z and COOH

| Example | B | Z | Q₃ | Yield (%) | ¹H NMR (d₆-DMSO) |
|---|---|---|---|---|---|
| 80 | $-C(CH_3)_2-$ | triazolyl: $-N$-$N=N$-ring with $=C(CH_3)$ | 3,4-dihydroxyphenyl | 51.3 | 1.61(s, 6H), 2.52(s, 3H), 3.70(m, 2H), 5.34(d, 1H), 5.75(m, 2H) |
| 81 | $-C(CH_3)_2-$ | $-S-$(thiadiazolyl with $CH_3$) | 3,4-dihydroxyphenyl | 63.4 | 1.58(s, 6H), 2.71(s, 3H), 3.73(m, 2H), 4.51(ABq, 2H), 5.28(d, 1H), 5.78–6.17(m, 1H), 6.81–7.63(m, 4H) |
| 82 | $-C(CH_3)_2-$ | $-S-$(tetrazolyl with N-$CH_2CH=CH_2$) | 3,4-dihydroxyphenyl | 58.7 | 1.57(s, 6H), 3.73(broad s, 2H), 4.48(m, 2H), 4.98–5.57(m, 6H), 5.77–6.18(m, 1H), 6.79–7.61(m, 4H) |
| 83 | $-C(CH_3)_2-$ | $-S-$(tetrazolyl with N-$CH_2CH_2OH$) | 3,4-dihydroxyphenyl | 57.3 | 1.58(s, 6H), 3.71(broad s, 2H), 4.24–4.84(m, 6H), 5.27(d, 1H), 5.76–6.20(m, 1H), 6.81–7.64(m, 4H) |
| 84 | $-C(CH_3)_2-$ | $-S-$(triazinyl-$CH_3$,OH,=O) | 3,4-dihydroxyphenyl | 54.3 | 1.58(s, 6H), 3.55–3.80(m, 5H), 4.55(m, 2H), 5.26(d, 1H), 5.77–6.14(m, 1H), 6.79–7.66(m, 4H) |

REFERENCE EXAMPLE 23

Synthesis of 2-(2-amino-1,3-thiazol-4-yl)-2-{1-[3-(3,4-dihydroxybenzoyl)carbazoyl]ethoxyimino}acetic acid.hydrochloride In 10 ml of methylene chloride was suspended 0.659 g (2 mmole) of 2-(2-amino-1,3-thiazol-4-yl)-2-(1-carbazoylethoxyimino)acetic acid tert-butyl ester, and to the suspension was added 2.5 g (12.3 mmole) of N,O-bis(trimethylsilyl)acetamide to form a solution. To the ice-cooled solution was added 0.565 g (2.2 mmole) of 3,4-diacetoxybenzoic acid chloride and the mixture was stirred for 1.5 hours under ice-cooling. The resulting mixture was poured into 150 ml of ether and to the mixture was added a small amount of methanol while stirring. Resulting precipitates were collected by filtration, washed with ether and then dried to obtain 1.05 g of 2-(2-amino-1,3-thiazol-4-yl)-2-{1-[3-(3,4-diacetoxybenzoyl)carbazoyl]ethoxyimino}acetic acid tert-butyl ester.hydrochloride. (Yield: 98.0%)

¹H NMR (d₆-DMSO) δ: 1.53 (broad s, 12H), 2.28 (s, 6H), 4.82 (q, 1H), 7.02–7.88 (m, 4H).

In 25 ml of methanol was dissolved 1.05 g (1.96 mmole) of the above hydrochloride, then 0.96 ml of 25% aqueous ammonia was added thereto and the mixture was stirred at room temperature for 40 minutes. The resulting mixture was concentrated, and the residue was dissolved in 100 ml of 30% THF-ethyl acetate, dried over anhydrous magnesium sulfate and then the solvent was distilled out after filtration. The resulting oily product was dissolved in 5 ml of trifluoroacetic acid and the solution was stirred at room temperature for 2 hours. Then, the resulting mixture was added dropwise into 100 ml of ether while vigorously stirring and resulting precipitates were collected by filtration, washed with ether and then dried to obtain 0.8 g of trifluoroacetic acid salt of the title compound. To 5 ml of ice-cooled methanol was added 0.77 g (5 mmole) of phosphorus oxychloride, and 0.8 g of the previously obtained trifluoroacetic acid salt was added thereto and the mixture was stirred for 10 minutes. The resulting mixture was added dropwise into 100 ml of ether while vigorously stirring and resulting precipitates were collected by filtration, washed with ether and then dried to obtain 0.55 g of the title compound. (Yield: 62.9%) Melting point: 157° to 159° C. (decomposed).

Structural formula:

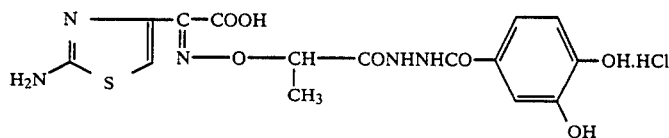

¹H NMR (d₆-DMSO+D₂O) δ: 1.46 (d, 3H), 4.85 (q, 1H), 6.70–7.43 (m, 4H).

EXAMPLE 85

Synthesis of 7-{2-[2-amino-1,3-thiazol-4-yl]-2-[1-(3-(3,4-dihydroxybenzoyl)carbazoyl)ethoxyimino]acetamido}-3-[(1,3,4-thiadiazol-2-yl)thiomethyl]-3-cephem-4-carboxylic acid.hydrochloride (I) In 5 ml of DMF were dissolved 0.5 g (1.12 mmole) of 2-(2-amino-1,3-thiazol-4-yl)-2-{1-[3-(3,4-dihydroxybenzoyl)carbazoyl]ethoxyimino}acetic acid.hydrochloride obtained in Reference example 23 and 0.556 g (1.12 mmole) of 7-amino-3-[(1,3,4-thiadiazol-2-yl)-thiomethyl]-3-cephem-4-carboxylic acid diphenylmethyl ester and the mixture was ice-cooled, and 0.276 g (1.34 mmole) of DCC was added thereto and stirred at room temperature for one hour. After filtration of the resulting mixture, to the filtrate was added the same amount of chloroform and the mixture was added dropwise into 200 ml of ether while vigorously stirring. Resulting precipitates were collected by filtration, washed with ether and then dried to obtain 1.01 g of the diphenylmethyl ester of the title compound. (Yield: 97.5%)

(II) A mixture comprising 4 ml of trifluoroacetic acid and 1 ml of anisole was ice-cooled, and to the mixture was added 0.3 g (0.32 mmole) of the diphenylmethyl ester obtained above and the mixture was stirred for 30 minutes. The resulting mixture was added dropwise into 80 ml of ether while vigorously stirring and resulting precipitates were collected by filtration, washed with ether and then dried to obtain 0.2 g of the title compound. (Yield: 82.4%) Melting point: 191° to 197° C. (decomposed).

Structural formula:

bazoyl-1-methylethoxyimino)acetic acid tert-butyl ester, and to the suspension was added 2.16 g (10.6 mmole) of N,O-bis(trimethylsilyl)acetamide to form a solution. To the ice-cooled solution was added 0.488 g (1.9 mmole) of 3,4-diacetoxybenzoic acid chloride and the mixture was stirred for one hour under ice-cooling. The resulting mixture was poured into 150 ml of ether and to the mixture was added a small amount of methanol while stirring. Resulting precipitates were collected by filtration, washed with ether and then dried to obtain 0.96 g of 2-(2-amino-1,3-thiazol-4-yl)-2-{1-[3-(3,4-diacetoxybenzoyl)carbazoyl]-1-methylethoxyimino}acetic acid tert-butyl ester.hydrochloride. (Yield: 97.9%)

¹H NMR (d₆-DMSO) δ: 1.54 (s, 15H), 2.26 (s, 6H), 6.90–7.78 (m, 4H).

In 25 ml of methanol was dissolved 0.96 g (1.7 mmole) of the above hydrochloride, then 1 ml of 25% aqueous ammonia was added thereto and the mixture was stirred at room temperature for 30 minutes. The resulting mixture was concentrated, and the residue was dissolved in 100 ml of 30% THF-ethyl acetate, dried over anhydrous magnesium sulfate and then the solvent was distilled out after filtration. The resulting oily product was dissolved in 10 ml of trifluoroacetic acid and the solution was stirred at room temperature for one hour. Then, the resulting mixture was added dropwise into 200 ml of ether while vigorously stirring and resulting precipitates were collected by filtration, washed with ether and then dried to obtain 0.88 g of trifluoroacetic acid salt of the title compound. To 10 ml of ice-cooled methanol was added 0.77 g (5 mmole) of phosphorus oxychloride, and 0.88 g of the previously obtained trifluoroacetic acid salt was added thereto and the mixture was stirred for 10 minutes. The resulting mixture was added dropwise into 150 ml of ether while vigorously

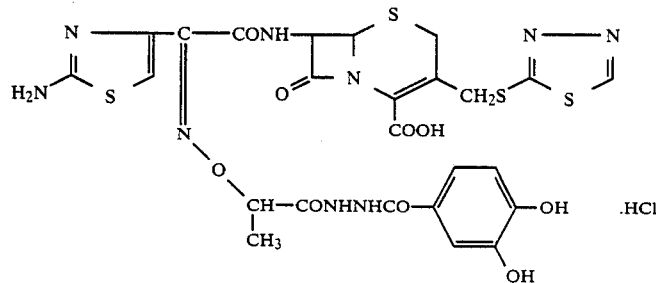

¹H NMR (d₆-DMSO) δ: 1.50 (d, 3H), 3.81 (broad s, 2H), 4.30 (m, 2H), 4.80 (q, 1H), 5.26 (q, 1H), 5.76–6.21 (m, 1H), 6.75–7.49 (m, 4H), 9.60 (s, 1H).

REFERENCE EXAMPLE 24

Synthesis of 2-(2-amino-1,3-thiazol-4-yl)-2-{1-[3-(3,4-dihydroxybenzoyl)carbazoyl]-1-methylethoxyimino}acetic acid.hydrochloride In 10 ml of methylene chloride was suspended 0.7 g (1.74 mmole) of 2-(2-amino-1,3-thiazol-4-yl)-2-(1-carstirring and resulting precipitates were collected by filtration, washed with ether and then dried to obtain 0.63 g of the title compound. (Yield: 80.6%)

Structural formula:

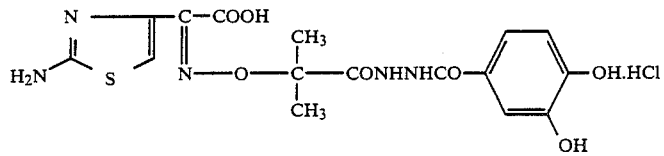

$^1$H NMR (d$_6$-DMSO) δ: 1.54 (s, 6H), 7.00–7.90 (m, 4H).

REFERENCE EXAMPLE 25

Synthesis of 2-(2-amino-1,3-thiazol-4-yl)-2-[3-(2-hydroxybenzoyl)-carbazoyl]methoxyiminio}acetic acid.hydrochloride In 20 ml of DMF were dissolved 3.15 g (10 mmole) of 2-(2-amino-1,3-thiazol-4-yl)-2-carbazoylmethoxyiminoacetic acid, 1.66 g (12 mmole) of salicylic acid and 1.62 g (12 mmole) of 1-hydroxybenzotriazole. To the ice-cooled solution was added 2.48 g (12 mmole) of DCC, and the mixture was stirred for one hour after removal of a cooling bath. After filtration of the resulting mixture, the filtrate was dissolved in 200 ml of ethyl acetate and then washed with water followed by washing with a saturated saline solution. Then, filtration and evaporation of the solvent were carried out. After the residue was dissolved in 15 ml of trifluoroacetic acid and the mixture was stirred at room temperature for 3 hours, the resulting mixture was added dropwise into 500 ml of ether while vigorously stirring. Resulting precipitates were collected by filtration, washed with ether and dried to obtain the trifluoroacetic acid salt of the title compound. To 30 ml of ice-cooled methanol were added 2.25 g (14.7 mmole) of phosphorus oxychloride and then the trifluoroacetic acid salt obtained above, and the mixture was stirred for 10 minutes. The resulting mixture was added dropwise into 1.4 liters of ether while vigorously stirring, and resulting precipitates were collected by filtration, washed with ether and then dried to obtain 4.02 g of the title compound. (Yield: 96.7%)

Structural formula:

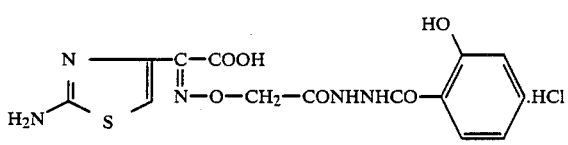

$^1$H NMR (d$_6$-DMSO) δ: 4.78 (s, 2H), 6.95–8.02 (m, 5H).

EXAMPLE 86

Synthesis of 7-}2-[2-amino-1,3-thiazol-4-yl]-2-[1-(3-(3,4-dihydroxybenzoyl)carbazoyl)-1-methylethoxyimino]acetamido}-3-[(1,3,4-thiadiazol-2-yl)thiomethyl]-3-cephem-4-carboxylic acid.hydrochloride (I) In 7 ml of DMF were dissoved 0.63 g (1.37 mmole) of 2-(2-amino-1,3-thiazol-4-yl)-2-{1-[3-(3,4-dihydroxybenzoyl)carbazoyl]-1-methylethoxyimino}acetic acid hydrochloride obtained in Reference example 24 and 0.68 g (1.37 mmole) of 7-amino-3-[(1,3,4-thiadiazol-2-yl)thiomethyl]-3-cephem-4-carboxylic acid diphenylmethyl ester and the mixture was ice-cooled, and 0.351 g (1.7 mmole) of DCC was added thereto and stirred at room temperature for 1.5 hours. After filtration of the resulting mixture, to the filtrate was added the same amount of chloroform and the mixture was added dropwise into 200 ml of ether while vigorously stirring. Resulting precipitates were collected by filtration, washed with ether and then dried to obtain 0.94 g of the diphenylmethyl ester of the title compound. (Yield: 73.1%)

(II) A mixture comprising 6 ml of trifluoroacetic acid and 1.5 ml of anisole was ice-cooled, and to the mixture was added 0.94 g (1 mmole) of the diphenylmethyl ester obtained above and the mixture was stirred for 30 minutes. The resulting mixture was added dropwise into 150 ml of ether while vigorously stirring and resulting precipitates were collected by filtration, washed with ether and then dried to obtain 0.7 g of the title compound. (Yield: 90.6%)

Structural formula:

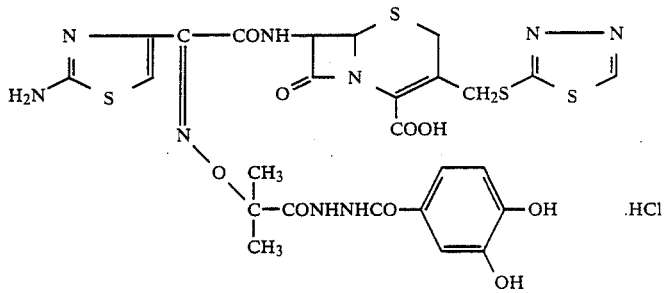

$^1$H NMR (d$_6$-DMSO) δ: 1.58 (s, 6H), 3.80 (broad s, 2H), 4.40 (m, 2H), 5.23 (d, 1H), 5.74–6.15 (m, 1H), 6.80–7.82 (m, 4H), 9.58 (s, 1H).

EXAMPLE 87

Synthesis of 7-{2-[2-amino-1,3-thiazol-4-yl]-2-[3-(3,4-diacetoxybenzoyl)carbazoyl]methoxyiminoacetamido}-3-[(5-methyl-1,3,4-thiadiazol-2-yl)thiomethyl]-3-cephem-4-carboxylic acid 1-ethoxycarbonyloxyethyl ester In 40 ml of DMF was dissolved 6.309 g (9.5 mmole) of 7-[2-(2-formylamino-1,3-thiazol-4-yl)-2-(3-formylcarbazoyl)methoxyiminoacetoamido]-3-[(5-methyl-1,3,4-thiadiazol-2-yl)thiomethyl]-3-cephem-4-carboxylic acid sodium salt and the mixture was ice-cooled, and 4.88 g (20 mmole) of 1-iododiethylcarbonate was added thereto and stirred at room temperature for 3 hours. To the resulting mixture was added 700 ml of ethyl acetate and the mixture was washed with water and then washed with a saturated saline solution, dried over anhydrous magnesium sulfate and the solvent was distilled out. The residue was purified through silica gel column chromatography (eluent: 5% to 10% methanol-chloroform). To 30 ml of ice-cooled methanol was added 0.92 g (6 mmole) of phosphorus oxychloride and then purified product through column, and the mixture was stirred for 1.5 hours under ice-cooling. The resulting mixture was added dropwise into 800 ml of ether while vigorously stirring and resulting precipitates were collected by filtration and dried. After the resulting product was dissolved in 30 ml of methylene chloride and ice-cooled, 25 ml (10 mmole) of N,O-bis(trimethylsilyl)acetamide was added thereto and the mixture was stirred for 10 minutes. Then, 0.9 g (3.5 mmole) of 3,4-diacetoxybenzoic acid chloride was added thereto and the mixture was stirred for one hour under ice-cooling. The resulting mixture was added dropwise into 800 ml of ether and resulting precipitates were collected by filtration, washed with ether and then dried to obtain 3.07 g of the title compound. (Yield: 35.5%)

Structural formula:

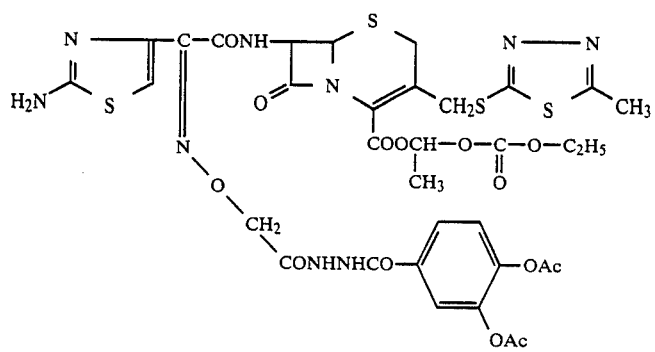

$^1$H NMR (d$_6$-DMSO) δ: 1.24 (t, 3H), 1.53 (d, 3H), 2.28 (s, 6H), 3.72 (broad s, 2H), 4.24 (m, 2H), 4.72 (m, 1H), 5.14 (d, 1H), 5.75–6.14 (m, 1H), 6.78–8.18 (m, 4H).

EXAMPLE 88

Synthesis of 7-{2-[2-amino-1,3-thiazol-4-yl]-2-[3-(3,4-dihydroxybenzoyl)carbazoyl]methoxyiminoacetamido}-3-pyridiniummethyl-3-cephem-4-carboxylic acid betaine In 70 ml of methylene chloride was suspended 2.159 g (5 mmole) of 2-(2-famino-1,3-thiazol-4-yl)-2-[3-(3,4-dihydroxybenzoyl)carbazoyl]methoxyiminoacetic acid hydrochloride and the mixture was ice-cooled, and then 3.49 g (25 mmole) of triethylamine and 2.54 ml (20 mmole) of trimethylchlorosilane (TMCS) were added thereto and stirred at room temperature for one hour to form a solution. The mixture was cooled to −40° C. and 0.38 ml of DMF and 0.55 g (2.8 mmole) of trichloromethylchloroformate (TCF) were successively added thereto. Then, the mixture was stirred at −30° C. for 0.5 hour and at −15° C. for 3 hours and thereafter cooled again to −35° C.

To the resulting mixture was added a solution obtained by mixing 1.826 g (5 mmole) of 7-amino-3-pyridiniummethyl-3-cephem-4-carboxylic acid betaine hydrochloride, 2.55 ml (10.4 mmole) of N,O-bis(trimethylsilyl)acetamide and 20 ml of methylene chloride and stirring them at room temperature for one hour, and the mixture was stirred for 1.5 hours while cooling with ice-salt bath. The resulting mixture was poured into 200 ml of ice-cooled water and stirred well. After distilled out the solvent, precipitates were removed by filtration. The filtrate was poured and adhered to a 500 ml of HP-20 column filled with water, washed with water and eluted by 50% methanol-water. After condensation of fractions containing the title compound, condensate was lyophilized to obtain 0.3 g of the title compound. (Yield: 8.9%)

Structural formula:

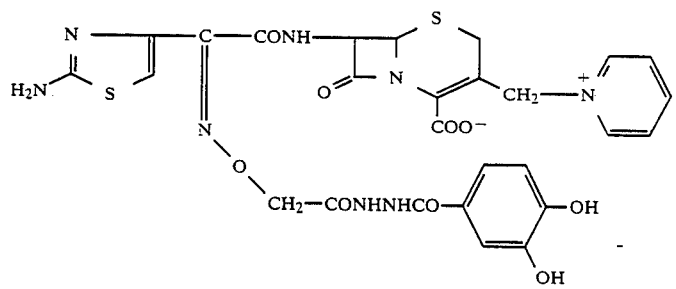

$^1$H NMR (d$_6$-DMSO) δ: 3.72 (broad s, 2H), 4.43 (m, 2H) 4.74 (broad s, 2H), 5.20 (d, 1H), 5.68–6.04 (m, 1H), 6.78–7.42 (m, 4H), 7.90–9.42 (m, 5H).

EXAMPLE 89

In the same manner as in Example 88, the compound shown below was obtained.
7-{2-[2-amino-1,3-thiazol-4-yl]-2-[1-(3-(3,4-dihydroxybenzoyl)carbazoyl)ethoxyimino]acetamido}-3-pyridiniummethyl-3-cephem-4-carboxylic acid betaine
Yield: 24.6%
Structural formula:

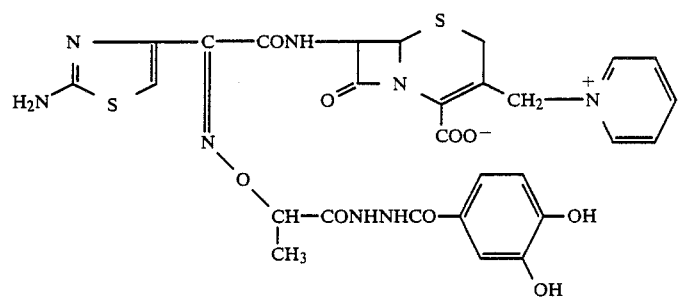

$^1$H NMR (d$_6$-DMSO) δ: 1.44 (d, 3H), 3.81 (broad s, 2H), 4.40 (m, 2H), 4.81 (q, 1H), 5.22 (d, 1H), 5.72–6.13 (m, 1H), 6.70–7.44 (m, 4H), 7.92–9.53 (m, 5H).

EXAMPLE 90

Synthesis of 7-{2-[2-amino-1,3-thiazol-4-yl]-2-[3-(3,4-dihydroxybenzoyl)carbazoyl]methoxyiminoacetamido}-3-(3-carboxypyridiniummethyl)-3-cephem-4-carboxylic acid betaine After a mixture comprising 1.679 g (2.5 mmole) of 7-{2-[2-amino-1,3-thiazol-4-yl]-2-[3-(3,4-dihydroxybenzoyl)carbazoyl]methoxyiminoacetamido}-3-acetoxymethyl-3-cephem-4-carboxylic acid, 1.616 g (13 mmole) of nicotinic acid, 4.5 g (30 mmole) of sodium iodide, 0.086 ml of phoshoric acid, 1.5 ml of water and 5 ml of acetonitrile was stirred for 9 hours in a bath of 65° to 75° C., insolubles were removed by filtration. The filtrate was added dropwise into 450 ml of acetone and resulting precipitates were collected by filtration, washed with acetone and then dried to obtain 0.79 g of the title compound. (Yield: 44.3%)
Structural formula:

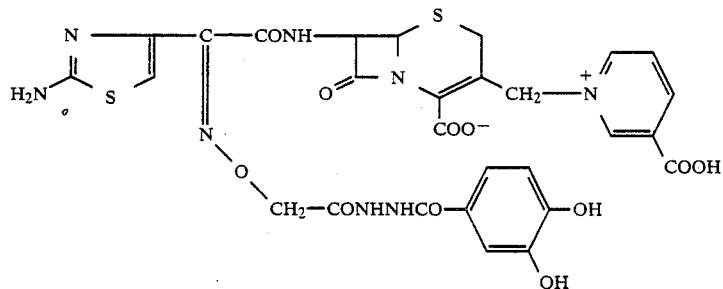

$^1$H NMR (d$_6$-DMSO) δ: 3.74 (broad s, 2H), 4.45 (m, 2H, 4.76 (broad s, 2H), 5.21 (d, 1H), 5.66–6.06 (m, 1H), 6.76–7.44 (m, 4H), 7.96–9.06 (m, 4H).

EXAMPLES 91 AND 92

In the same manner as in Example 90, the compound shown by the following formula was prepared. The results are shown in Table 7.

TABLE 7

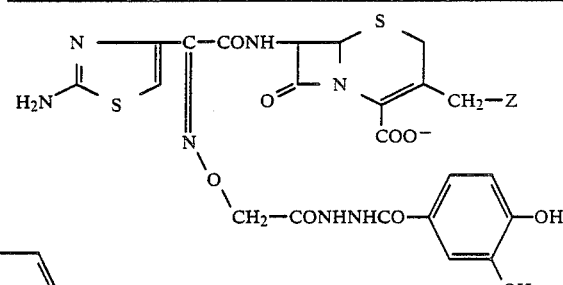

| Example | Z | Yield (%) | $^1$H NMR (d$_6$-DMSO)δ |
|---|---|---|---|
| 91 | —$^+$N⌬—COOH | 61.1 | 3.75 (broad s, 2H), 4.44(m, 2H), 4.77 (broad s, 2H), 5.24(d, 1H), 5.65~6.06(m, 1H), 6.74~7.50(m, 4H), 7.78~8.96(m, 4H) |
| 92 | —$^+$N⌬—CONH$_2$ | 15.2 | 3.76 (broad s, 2H), 4.46(m, 2H), 4.78 (broad s, 2H), 5.26(d, 1H), 5.64~6.02(m, 1H), 6.72~7.53(m, 4H), 7.83~9.04(m, 4H) |

REFERENCE EXAMPLE 26

Synthesis of 6-[2-(2-amino-1,3-thiazol-4-yl)-2-carbazoylmethoxyiminoacetamido]-penicillanic acid.dihydrochloride To 10 ml of ice-cooled DMF was added 1.23 g (8 mmole) of phosphorus oxychloride under stirring and stirring was continued at 40° C. for 30 minutes. After cooling the mixture to −30° C., 1.262 g (4 mmole) of 2-(2-formylamino-1,3-thiazol-4-yl)-2-(3-formylcarbazoyl)methoxyiminoacetic acid was added thereto and the mixture was stirred at −20° to −30° C. for one hour. A mixture comprising 0.952 g (4.4 mmole) of 6-aminopenicillanic acid (6-APA), 20 ml of methylene chloride and 1.79 g (8.8 mmole) of N,O-bis(trimethylsilyl)acetamide was stirred at room temperature for 30 minutes and cooled to −40° C. To the thus obtained mixture was added the previously obtained mixture for 5 minutes under cooling, and the mixture was stirred at −40° C. for 3 hours. The resulting mixture was added dropwise into 100 ml of ice-cooled water and simultaneously a 5% aqueous sodium hydrogencarbonate solution was added thereto to adjust to pH 7. After separation of a methylene chloride layer, an aqueous layer washed with methylene chloride was adjusted to pH 5 with a 2N-hydrochloric acid and distilled out methylene chloride dissolved in the aqueous layer. The remaining aqueous layer was adjusted to pH 2 with a 2N-hydrochloric acid and saturated with salt. Then, the aqueous layer was extracted with 100 ml of THF, the extract was dried over anhydrous magnesium sulfate and distilled out the solvent. To the oily residue were added 50 ml of water and a 5% aqueous sodium hydrogencarbonate solution to dissolve it at pH 7, and the solution was adhered to a column filled with 100 ml of HP-20, washed with water and eluted with 50% methanol-water. Distillation of methanol from the eluant, followed by lyophilization of the resulting aqueous solution yielded powder. To 5 ml of ice-cooled methanol was added 0.28 g (183 mmole) of phosphorus oxychloride, and then the previously obtained powder was added thereto and the mixture was stirred for one hour under ice-cooling. The resulting mixture was added dropwise into 150 ml of ether while vigorously stirring, and resulting precipitates were collected by filtration, washed with ether and dried to obtain 0.57 g of the title compound as a white powder. (Yield: 26.9%)

Melting point: 178° to 185° C. (decomposed).
Structural formula:

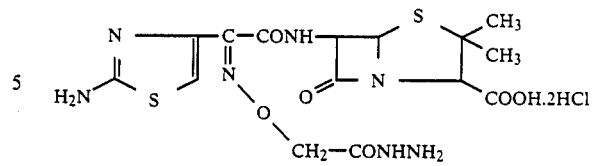

$^1$H NMR (d$_6$-DMSO) δ: 1.38 (s, 3H), 1.58 (s, 3H), 4.12 (s, 1H), 4.72 (broads, 2H), 5.30–5.72 (m, 2H), 7.28 (s, 1H).

EXAMPLE 93

Synthesis of 6-{2-(2-amino-1,3-thiazol-4-yl)-2-[3-(3,4-dihydroxybenzylidene)carbazoyl]methoxyiminoacetamido}penicillanic acid.hydrochloride To 5 ml of methanol were dissolved 0.4 g (0.754 mmole) of 6-[2-(2-amino-1,3-thiazol-4-yl)-2-carbazoylmethoxyiminoacetamido]penicillanic acid.dihydrochloride obtained in Reference example 26 and 0.11 g (0.8 mmole) of 3,4-dihydroxybenzaldehyde and the mixture was stirred at room temperature for one hour. The resulting mixture was added dropwise into 150 ml of ether while vigorously stirring, resulting precipitates were collected by filtration, washed with ether and then dried to obtain 0.4 g of the title compound as a pale yellow powder. (Yield: 86.4%) Melting point: 177° to 183° C. (decomposed).

Structural formula:

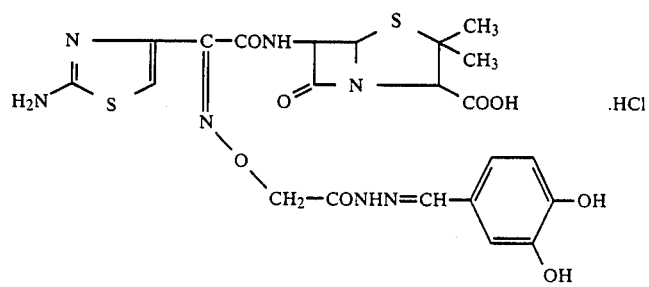

$^1$H NMR (d$_6$-DMSO) δ: 1.37 (s, 3H), 1.59 (s, 3H), 4.13 (s, 1H), 4.73 (broad s, 2H), 5.22–5.52 (m, 2H), 6.82–7.34 (m, 4H), 8.07 (d, 1H).

EXAMPLE 94

Synthesis of sodium 6-{2-[2-amino-1,3-thiazol-4-yl]-2-[3-(3,4-dihydroxybenzoyl)carbazoyl]methoxyiminoacetamido}penicillanate In 200 ml of methylene chloride was suspended 5.8 g (13.43 mmole) of 2-(2-amino-1,3-thiazol-4-yl)-2-[3-(3,4-dihydroxybenzoyl)carbazoyl]methoxyiminoacetic acid.hydrochloride and the suspension was ice-cooled, 9.4 ml (67.15 mmole) of triethylamine and 6.82 ml of TMCS were added thereto and the mixture was stirred for one hour. After the resulting mixture was cooled to −40° C., 1 ml of DMF and 0.97 ml (8.06 mmole) of trichloromethylchloroformate were successively added thereto and the mixture was stirred at −15° to −20° C. for 2 hours and then cooled again to −40° C.

To the thus obtained mixture was added a solution obtained by stirring a mixture comprising 3.244 g (15 mmole) of 6-APA, 100 ml of methylene chloride and 6.1 g (30 mmole) of N,O-bis-(trimethylsilyl)acetamide at room temperature for one hour, and the mixture was stirred at −20° C. for 1.5 hours, and then for 0.5 hour while cooling with an ice-salt bath. The resulting mixture was adjusted to pH about 2 with a 5% aqueous sodium hydrogen-carbonate solution while pouring it into 200 ml of ice-cooled water. Precipitates were collected by filtration, washed with water and then with ether, and dried. After the obtained crude product was dissolved in 30 ml of DMF, 2.5 g of sodium 2-ethylhexanoate was added thereto and the mixture was stirred. After filtration, the filtrate was added dropwise into 800 ml of a 10% methanol-ether mixture. Resulting precipitates were collected by filtration, washed with a 10% methanol-ether and then with ether, and dried. This product was dissolved in 100 ml of water. After filtration of the solution, the filtrate was adhered to a column filled with 400 ml of HP-20, washed with water and eluted with 20% methanol-water. Fractions containing the title compound were condensed and lyophilized to obtain 2.12 g of the title compound. (Yield: 25.68%)
Structural formula:

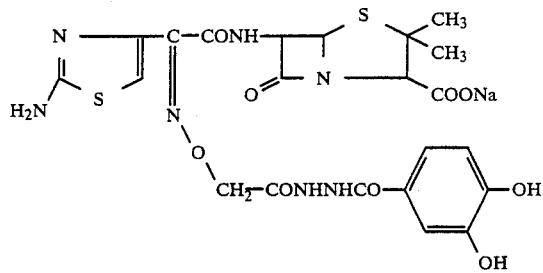

$^1$H NMR (d$_6$-DMSO) δ: 1.52 (s, 3H), 1.54 (s, 3H), 4.08 (s, 1H), 4.71 (broad s, 2H), 5.48–5.72 (m, 2H), 6.81–7.58 (m, 4H).

REFERENCE EXAMPLE 27

Synthesis of 2-(2-formylamino-1,3-thiazol-4-yl)-2-(3-t-butoxycarbonylcarbazoylamino)acetic acid ethyl ester A suspension comprising 6.44 g (0.1014 mole) of N,N'-carbonyldiimidazole suspended in 70 ml of N,N-dimethylformamide was stirred under ice-cooling to set at 0° C., and to the mixture was added 13.40 g (0.1014 mole) of t-butylcarbazate by dividing it into a small amount while maintaining the temperature of the mixture to 20° C. After completion of the addition, the mixture was further stirred for 2 hours under ice-cooling and a solution of 15.5 g (67.6 mmole) of 2-amino-2-(2-formylamino-1,3-thiazol-4-yl)acetic acid ethyl ester dissolved in 25 ml of DMF was added thereto for 5 minutes, and stirring was continued under ice-cooling for 30 minutes and at room temperature for 15 hours.

The resulting mixture was poured into 800 ml of water, neutralized with 2N hydrochloric acid to pH 4 and extracted five times with 200 ml of chloroform. The obtained extracts was washed three times with 300 ml of water, dried over anhydrous magnesium sulfate and distilled the solvent under reduced pressure. The resulting amorphous residue was ground with diisopropyl ether and filtrated to obtain 19.4 g (Yield: 74%) of 2-(2-formylamino-1,3-thiazol-4-yl)-2-(3-t-butoxycarbonylcarbazoylamino)acetic acid ethyl ester as a pale yellow crystal. Melting point: 85° C. (decomposed).
Structural formula:

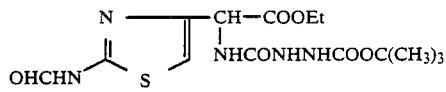

$^1$H NMR (CDCl$_3$) δ: 1.20 (3H, t, J=8 Hz), 1.40 (9H, s), 4.19 (2H, q, J=8), 5.60 (1H, d, J=8) (which becomes singlet with D$_2$O), 6.95 (1H, broad s, J=8) (which is disappeared with D$_2$O), 6.99 (1H, s), 7.56 (1H, broad s) (which is disappeared with D$_2$O), 7.88 (1H, broad s) (which is disappeared with D$_2$O), 8.58 (1H, s).

REFERENCE EXAMPLE 28

Synthesis of 2-(2-formylamino-1,3-thiazol-4-yl)-2-(3-t-butoxycarbonylcarbazoylamino)acetic acid In 85.6 ml of 0.5M aqueous sodium hydroxide solution was suspended 8.3 g (21.42 mmole) of the compound obtained in Reference example 27, and the mixture was stirred at room temperature for 45 minutes. To the obtained mixture was added 150 ml of ethyl acetate, and the mixture was adjusted to pH 3 with the addition of 2N hydrochloric acid and an aqueous layer was extracted twice with 100 ml of ethyl acetate. The obtained organic layers were dried over anhydrous magnesium sulfate, the solvent was distilled under reduced pressure, and the residue was ground with ether, filtered and dried to obtain 6.99 g (Yield: 91%) of 2-(2-formylamino-1,3-thiazol-4-yl)-2-(3-t-butoxycarbonylcarbazoylamino)acetic acid as a white crystal. Melting point: 121° C. (decomposed)
Structural formula:

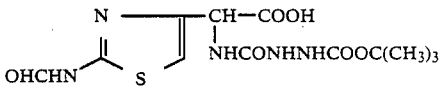

$^1$H NMR (CDCl$_3$+d$_6$-DMSO) δ: 1.22 (3H, t, J=7 Hz), 1.42 (9H, s), 4.07 (2H, q, J=7), 5.48 (1H, d, J=8) (which becomes s with D$_2$O), 6.72 (1H, d, J=8) (which is disappeared with D$_2$O), 7.01 (1H, s), 7.82 (1H, s) (which is disappeared with D$_2$O), 8.02 (1H, s) (which is disappeared with D$_2$O), 8.45 (1H, s).

REFERENCE EXAMPLE 29

Synthesis of 2-(2-formylamino-1,3-thiazol-4-yl)-2-(3-t-butoxycarbonylcarbazoylamino)acetic acid ethyl ester.hydrochloride To 20 ml of methanol was added 0.96 g (10.3 mmole) of phosphorus oxychloride under ice-cooling, and the mixture was stirred and set to 0° C. To the mixture was added little by little dividing 2.00 g (5.16 mmole) of the product obtained in Reference example 27. The mixture was stirred at the same temperature for 1.5 hours, poured into 200 ml of ether while stirring and precipitates were collected by filtration to obtain a white crystal of the title compound 1.80 g (Yield: 88%) as a hydrochloride.
Structural formula:

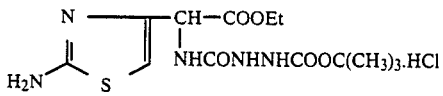

$^1$H NMR (CDCl$_3$+d$_6$-DMSO) δ: 1.30 (3H, t, J=8 Hz), 1.40 (9H, s), 4.11 (2H, q, J=8), 5.34 (1H, d, J=6) (which becomes singlet with substitution of D$_2$O), 6.33 (1H, s).

REFERENCE EXAMPLE 30

Synthesis of 2-(1-amino-1,3-thiazol-4-yl)-2-(3-t-butoxycarbonylcarbazoylamino)acetic acid To 0.75 g (1.89 mmole) of the product according to Reference example 29 was added 5.7 ml of a 1N aqueous sodium hydroxide solution and the mixture was stirred at room temperature for one hour. After dilution of the mixture with 20 ml of water, the mixture was neutralized with 2N hydrochloric acid and adjusted to pH 3, saturated by the addition of salt and extracted twice with 25 ml of tetrahydrofuran. The extracts were washed with 15 ml of a saturated saline solution, dried over anhydrous magnesium sulfate and evaporated to obtain residue. Ether was added to the residue to be powdered to obtain 0.35 g of the title compound. (Yield: 56%) Melting point: 123° C. (decomposed).
Structural formula:

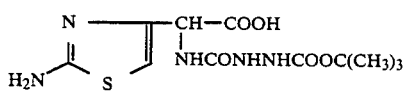

$^1$H NMR (d$_6$-DMSO) δ: 1.40 (9H, s), 5.09 (1H, d, J=9 Hz) (which becomes singlet with substitution of D$_2$O), 6.45 (1H, s).

REFERENCE EXAMPLE 31

Synthesis of 6-[2-(2-formylamino-1,3-thiazol-4-yl)-2-(3-t-butoxycarbonylcarbazoylamino)acetamido]penicillanic acid After dissolving in 40 ml of THF a mixture comprising 2.00 g (5.565 mmole) of the compound obtained in Reference example 28 and 0.752 g (5.565 mmole) of 1-hydroxybenzotriazole, the solution was ice-cooled to −10° C. and 1.15 g (5.565 mmole) of DCC was added thereto all at once. The mixture was stirred at −10° C. to 0° C. for 3 hours.

During this stage, to 50 ml of methylene chloride suspension suspended 1.20 g (5.565 mmole) of 6-APA was added 1.94 ml (13.9 mmole) of triethylamine and the mixture was stirred at room temperature to form a solution. The resulting solution was added dropwise to the previously prepared mixture for 5 minutes and the mixture was stirred at 0° C. for 2 hours.

The resulting mixture was filtered, and the residue was washed with a small amount of THF. The filtrates were combined and evaporated, the residue was distributed to 100 ml of 2% aqueous sodium hydrogencarbonate solution and 70 ml of ethyl acetate, and was extracted with 30 ml of 2% aqueous sodium hydrogencarbonate solution further from the organic layer. The aqueous layers were combined, neutralized with 2N hydrochloric acid and adjusted to pH 3.5. The mixture was extracted twice with 100 ml of ethyl acetate, the extracts were dried over anhydrous magnesium sulfate and evaporated. To the residue of which a part was crystallized was added a mixed solution comprising 100 ml of ether and 100 ml of isopropyl ether, and insolubles were removed by filtration yielded 1.82 g of crude crystals containing 1-hydroxybenzotriazole. The thus obtained product was purified through silica gel column chromatography (Silicagel 60 Merck; 50 g) by eluting it with chloroform-methanol-formic acid (50:5:2) to obtain 0.860 g of white crystals of monoformic acid salt of the title compound. (Yield: 25.6%)
Melting point: 194° C. (decomposed).
Structural formula:

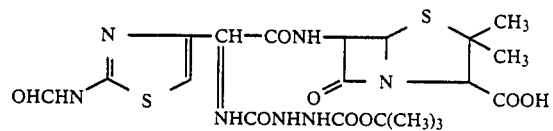

$^1$H NMR (CDCl$_3$+d$_6$-DMSO) δ: 1.45 (9H, s), 1.49, 162 (each 3H, s), 4.78 (7H, s), 5.56 (3H, s) (which changes with D$_2$O substitution), 7.04 (1H, s), 8.07 (1H, s) (HCOOH), 8.46 (1H, s).

REFERENCE EXAMPLE 32

Synthesis of 6-[2-(2-formylamino-1,3-thiazol-4-yl)-2-carbazoylaminoacetamido]penicillanic acid.trifluoroacetic acid salt To 0.800 g (1.44 mmole) of the product obtained in Reference example 31 were added successively 1 ml of anisole and 5 ml of trifluoroacetic acid and the mixture was stirred for one hour under ice-cooling and further for one hour at room temperature. The resulting mixture was added dropwise into 100 ml of stirring ether, and precipitates were collected by filtration, vacuum dried to obtain 0.814 g of the title compound as its trifluoroacetic acid salt. (Yield: 99.3%) Melting point: 119° C. (decomposed).
Structural formula:

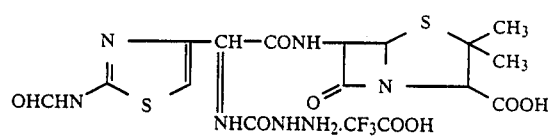

$^1$H NMR (d$_6$-DMSO) δ: 1.42 (3H, s), 1.49 (3H, s), 3.14 (1H, s), 5.00–5.80 (3H, m), 7.10 (1H, s), 8.42 (1H, s).

EXAMPLE 95

Synthesis of 6-[2-(2-formylamino-1,3-thiazol-4-yl)-2-{3-(3,4-dihydroxybenzylidene)carbazoylamino}acetamido]penicillanic acid In 3 ml of methanol was dissolved 300 ml of the compound according to Reference example 32, and 109 mg (0.787 mmole) of 3,4-dihydroxybenzaldehyde was added thereto at room temperature and the mixture was stirred for one hour at the same temperature. The resulting solution was added to 60 ml of ether while stirring, and precipitates were collected by filtration and vacuum dried to obtain 174 mg (Yield: 57.4%) of the aimed white powder.
Melting point: 158° C. (decomposed).
Structural formula:

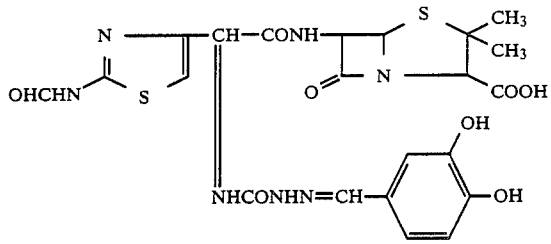

$^1$H NMR (d$_6$-DMSO) δ: 1.39 (3H, s), 1.53 (3H, s), 3.54 (1H, s), 4.8–5.9 (3H, m), 6.78 (1H, s), 7.11 (2H, m), 7.41 (1H, m), 7.72 (1H, s), 8.43 (1H, s).

EXAMPLE 96

Synthesis of 6-[2-(2-amino-1,3-thiazol-4-yl)-2-{3-(3,4-dihydroxybenzylidene)carbazoylamino}acetamido]penicillanic acid.hydrochloride In 3 ml of methanol was added under ice-cooling 0.20 ml (2.15 mmole) of phosphorus oxychloride and the mixture was stirred for 5 minutes. Then, 130 mg (0.225 mmole) of the compound according to Example 92 was added thereto and the mixture was stirred at the same temperature for one hour. The resulting mixture was added dropwise to 50 ml of ether while stirring, and precipitates were collected by filtration and vacuum dried to obtain 95 mg (Yield: 72.0%) of the title compound as a white powder.

Melting point: 163° C. (decomposed).
Structural formula:

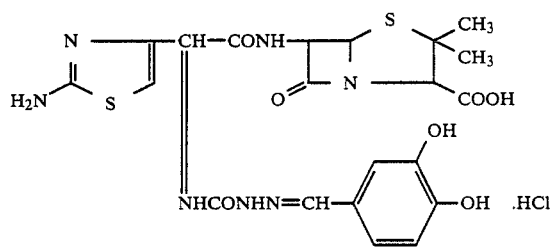

$^1$H NMR (d$_6$-DMSO) δ: 1.55 (6H, s), 3.72 (1H, s), 5.0–5.9 (3H, m), 6.87 (3H, m), 7.16 (1H, m), 7.95 (1H, s).

REFERENCE EXAMPLE 33

Synthesis of 7-[2-(2-amino-1,3-thiazol-4-yl)-2-(3-t-butoxycarbonylcarbazoylamino)acetamido]cephalosporanic acid diphenylmethyl ester 300 mg 0.905 mmole) of the compound according to Reference example 30 and 397 mg (0.905 mmole) of 7-ACA diphenylmethyl ester in 3 ml of DMF was stirred under ice-cooling, and to the mixture was added 205 mg (0.996 mmole) of DCC and stirred for one hour at the same temperature and further for one hour at room temperature. After a small amount of ethyl acetate was added thereto, the mixture was filtered to remove insolubles and washed with ethyl acetate. The filtrate and washing solution were combined and added dropwise into 150 ml of ether while stirring. Resulting precipitates were collected by filtration and vacuum dried to obtain 342 mg of the title compound as a pale orange powder. (Yield: 50.3%)

Structural formula:

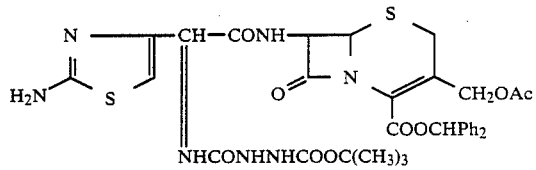

$^1$H NMR (CDCl$_3$) δ: 1.41 (9H, s), 1.96 (3H, s), 3.35 (2H, m), 4.83 (2H, m), 5.65 (2H, m), 6.83 (1H, m), 6.91 (2H, s), 7.38 (10H, s).

REFERENCE EXAMPLE 34

Synthesis of 7-[2-(2-formylamino-1,3-thiazol-4-yl)-2-(3-t-butoxycarbonylcarbazoylamino)acetamido]-3-[(2-methyl-1,3,4-thiadiazol-5-yl)thiomethyl]-3-cephem-4-carboxylic acid diphenylmethyl ester In 4 ml of DMF solution containing a mixture comprising 670 mg (1.86 mmole) of the compound according to Reference example 28 and 952 mg (1.86 mmole) of 7-amino-3-(2-methyl-1,3,4-thiazol-5-yl)thiomethyl-3-cephem-4-carboxylic acid diphenylmethyl ester was added under ice-cooling 390 mg (1.89 mmole) of N,N'-dicyclohexylcarbodiimide (DCC) and the mixture was stirred at the same temperature for 30 minutes and at room temperature for one hour. To the mixture was added 5 ml of ethyl acetate, the mixture was stirred for 5 minutes and then filtered to remove insolubles, and the residue was washed with a small amount of the same solvent. The filtrate and washing solution were combined and added dropwise into 170 ml of ether while stirring, and precipitated solids were collected by filtration and vacuum dried to obtain 1.39 g (Yield: 88%) of a white powder of the title compound.

Melting point: 150° C. (decomposed).
Structural formula:

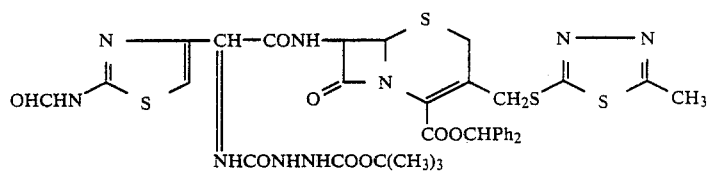

$^1$H NMR (CDCl$_3$) δ: 1.39 (9H, s), 2.62 (3H, s), 3.58 (2H, m), 4.25 (2H, m), 4.87 (1H, m), 5.71 (2H, m), 6.91 (2H, s), 7.30 (10H, s), 8.47 (1H, s).

REFERENCE EXAMPLES 35 TO 39

In the same manner as in Reference example 34, the compounds represented by the following formula were prepared. The results are shown in Table 8.

TABLE 8

Structure (header):
N═C(OHCHN)—S—CH═CH—CONH—[β-lactam-cephem]—CH₂—T, with NHCONHNHCOOC(CH₃)₃ substituent and COOH.

| Reference example | T | Yield (%) | NMR (CDCl₃ + DMSO—d₆) δ (ppm) |
|---|---|---|---|
| 35 | -S-[1,3,4-thiadiazol-2-yl]-H | 98% | 1.37(9H, s), 3.52(2H, m), 4.33(2H, m), 4.85(1H, m), 5.60(2H, m), 6.90(2H, s), 7.30(10H, s), 8.50(1H, s) |
| 36 | -S-[1-methyl-1,2,4-triazol-3-yl] (N-CH₃) | 93% | 1.38(9H, s), 3.55(2H, m), 4.00(3H, s), 4.30(2H, m), 4.85(1H, m), 5.65(2H, m), 6.91(2H, s), 7.30(10H, s), 8.50(1H, s) |
| 37 | -S-[1-(CH₂CO₂CHφ₂)-1,2,4-triazol-3-yl] | 99% | 1.38(9H, s), 3.45(2H, m), 4.15(2H, m), 4.78(1H, m), 5.01(2H, s), 6.84(3H, s), 7.31(20H, s), 8.36(1H, s) |
| 38 | -S-[triazinone, N-CH₃, OH] | 70% | 1.43(9H, s), 3.28(3H, s), 3.45(2H, m), 4.07(2H, m), 5.00(1H, m), 5.37(1H, m), 5.70(1H, m), 6.45(1H, s), 6.91(1H, s), 7.40(10H, s), 8.51(1H, s) |
| 39 | -S-[triazinone, N-CH₃, OCHφ₂] | 79% | 1.36(9H, s), 3.41(3H, s), 3.56(2H, m), 4.18(2H, m), 4.77(1H, m), 5.65(2H, m), 6.67(1H, s), 6.89(2H, s), 7.23(20H, s), 8.34(1H, s) |

Note: measured by using CDCl₃

REFERENCE EXAMPLE 40

Synthesis of 7-[2-(2-amino-1,3-thiazol-4-yl)-2-(3-t-butoxycarbonylcarbazoylamino)acetamido]-3-[(2-methyl-1,3,4-thiadiazol-5-yl)thiomethyl]-3-cephem-4-carboxylic acid diphenylmethyl ester.hydrochloride After 15 ml of methanol was ice-cooled to set 5° C., 0.73 ml (7.82 mmole) of phosphorus oxychloride was added thereto and the mixture was stirred for 5 minutes. To the resulting mixture was added 3.33 g (3.91 mmole) of the compound according to Reference example 34, and the mixture was further stirred for 1.5 hours under ice-cooling. The resulting mixture was added into 200 ml of ether while stirring, precipitated solids were collected by filtration and the residue was vacuum dried to obtain 3.30 g (Yield: 98%) of a white powder of the title compound. Melting point: 119° C. (decomposed).

Structural formula:

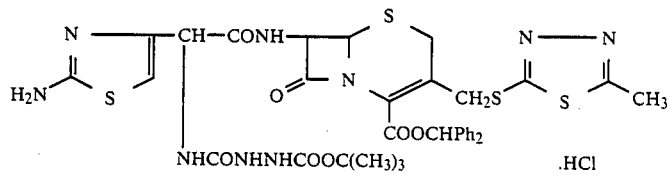

¹H NMR (CDCl₃+d₆-DMSO) δ: 1.41 (9H, s), 2.66 (3H, s), 3.77 (2H, m), 4.39 (2H, m), 5.15 (1H, m), 5.73 (2H, m), 6.96 (2H, s), 7.41 (10H, s).

REFERENCE EXAMPLES 41 TO 45

In the same manner as in Reference example 40 by treating the compounds according to Reference examples 35 to 39, the compounds represented by the following formula were prepared. The results are shown in Table 9.

TABLE 9

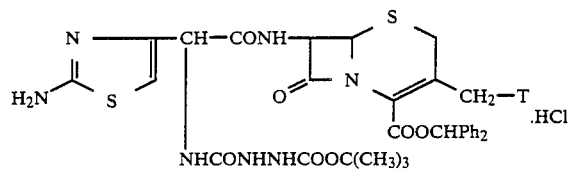

| Reference example | Starting material (Ref. ex. No.) | T | Yield (%) | Melting point | NMR δ (ppm) |
|---|---|---|---|---|---|
| 41 | 35 | ![structure] -S-<(N-N/S)>-H | 97 | 178° C. (decomposed) | (CDCl$_3$ + DMSO—d$_6$) 1.40(9H, s), 3.72(2H, m), 4.38(2H, m), 5.03(1H, m), 5.66(2H, s), 6.89(2H, s), 7.30(10H, s), 9.14(1H, s) |
| 42 | 36 | -S-<(N-N/N-N)>-CH$_3$ | 95 | — | — |
| 43 | 37 | -S-<(N-N/N-N)>-CH$_2$CO$_2$CH$\phi_2$ | 73 | — | (CDCl$_3$) 1.39(9H, s), 3.40(2H, m), 4.11(2H, m), 4.86(1H, m), 5.00(2H, m), 5.60(2H, m), 5.60(2H, m), 6.34(1H, s), 6.83(2H, s), 7.25(20H, s) |
| 44 | 38 | -S-<(N-N/CH$_3$)>-OH (=O) | 90 | — | (CDCl$_3$ + DMSO—d$_6$) 1.42(9H, s), 3.29(3H, s), 3.61(2H, m), 4.05(2H, m), 5.62(1H, m), 5.37(1H, m), 5.70(1H, m), 6.42(1H, s), 6.92(1H, s), 7.32(10H, s) |
| 45 | 39 | -S-<(CH$_3$-N-N/N)>-OCH$\phi_2$ (=O) | 90 | — | — |

REFERENCE EXAMPLE 46

Synthesis of 7-[2-(2-amino-1,3-thiazol-4-yl)-2-carbazoylaminoacetamido]-3-[(2-methyl-1,3,4-thiadiazol-5-yl)thiomethyl]-3-cephem-4-carboxylic acid.dihydrochloride After 15 ml of trifluoroacetic acid and 3 ml of anisole were ice-cooled to 0° C., to the mixture was added 3.00 g (3.49 mmole) of the compound according to Reference example 40 and the mixture was stirred at the same temperature for one hour. After to the resulting mixture was added 1 ml of conc. hydrochloric acid, the mixture was stirred at the same temperature for one minute and added into 250 ml of ether, and the mixture was further stirred for 10 minutes. Precipitated solids were collected by filtration and vacuum dried to obtain 2.15 g (Yield: 98%) of a pale yellow solid of the title compound as dihydrochloride.

Structural formula:

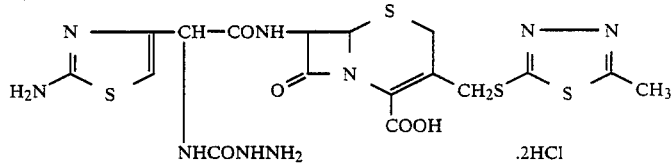

$^1$H NMR (d$_6$-DMSO) δ: 2.67 (3H, s), 3.68 (2H, m), 4.36 (2H, m), 5.05 (1H, m), 5.56 (2H, m), 6.70 (1H, s).

REFERENCE EXAMPLES 47 TO 52

In the same manner as in Reference example 46 by treating the compounds according to Reference example 33 and Reference examples 41 to 45, the compounds represented by the following formula were prepared. The results are shown in Table 10.

ybenzaldehyde and the mixture was stirred at room temperature for 1.5 hours. The resulting mixture was

TABLE 10

Structure:

$H_2N-C(=N)-S-CH=CH-CH(NHCONHNH_2)-CONH-$ [β-lactam]$-CH_2-T \cdot 2HCl$

| Reference example | Starting material (Ref. ex. No.) | T. | Yield (%) | Melting point (°C.) | NMR (DMSO—$d_6$), δ (ppm) |
|---|---|---|---|---|---|
| 47 | 33 | $-S-\underset{S}{\overset{N-N}{\parallel}}$ (1,3,4-thiadiazol-2-ylthio) | 99.5 | 123 (decomposed) | 3.70(9H, m), 4.43(2H, m), 5.08(1H, m), 5.59(2H, m), 6.77(1H, s), 9.58(1H, s) |
| 48 | 41 | $-S-\underset{N(CH_3)}{\overset{N-N}{\parallel}}N$ (1-methyltetrazol-5-ylthio) | 91 | — | 3.68(2H, m), 3.96(3H, s), 4.33(2H, m), 5.06(1H, m), 5.55(2H, m), 6.60(1H, s) |
| 49 | 42 | $-S-\underset{N(CH_2CO_2H)}{\overset{N-N}{\parallel}}N$ | 94 | 126 (decomposed) | 3.66(2H, m), 4.33(2H, m), 5.08(2H, m), 6.29(2H, s), 5.64(1H, m), 6.50(1H, s) |
| 50 | 43 | $-S-\underset{N(CH_3)}{\overset{N=N}{\parallel}}\underset{O}{\overset{}{C}}-OH$ | 99 | 127 (decomposed) | 3.28(1H, s), 3.62(2H, m), 4.09(2H, m), 5.07(1H, m), 5.31(1H, m), 5.65(1H, m), 6.48(1H, s) |
| 51 | 44 | —OCOCH$_3$ | 98 | — | 1.98(3H, s), 4.73(2H, m), 5.60(2H, m), 6.04(1H, m), 6.67(1H, s) |
| 52 | 45 | $CH_3-N-\underset{N}{\overset{N}{\parallel}}\underset{O}{\overset{}{C}}-OH$, $-S-$ | 85 | — | 3.15(3H, s), 3.3~4.4(4H, m) 5.02(1H, m), 5.56(2H, m), 6.76(1H, s) |

EXAMPLE 97

Synthesis of 7-[2-(2-amino-1,3-thiazol-4-yl)-2-{3-(3,4-dihydroxybenzylidene)carbazoylamino}acetamido]-3-[(2-methyl-1,3,4-thiadiazol-5-yl)thiomethyl]-3-cephem-4-carboxylic acid.hydrochloride To 3 ml methanol solution containing 200 mg (0.317 mmole) of the compound obtained in Reference example 46 was added 50 mg (0.362 mmole) of 3,4-dihydroxybenzaldehyde and the mixture was stirred at room temperature for 1.5 hours. The resulting mixture was added dropwise into 70 ml of ether while stirring, precipitated solids were collected by filtration and vacuum dried to obtain 195 mg (Yield: 86%) of a white powder of the title compound.

Structural formula:

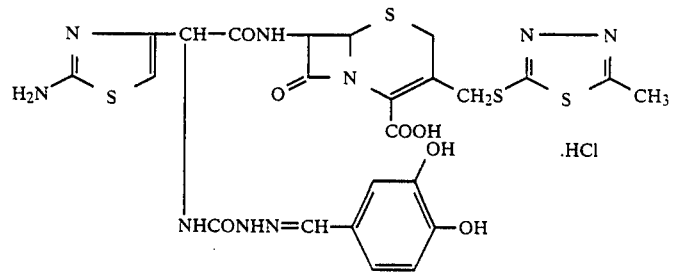

$^1$H NMR ($d_6$-DMSO) δ: 2.67 (3H, s), 3.65 (2H, m), 4.37 (2H, m), 5.10 (1H, m), 5.62 (2H, m), 6.83 (3H, broad s), 7.14 (1H, broad s), 7.75 (1H, s), 9.45 (1H, 1H, d, J=9).

EXAMPLES 98 TO 113

In the same manner as in Example 97, hydrochlorides of the β-lactam compounds represented by the following formula were prepared. The results are shown in Table 11.

TABLE 11

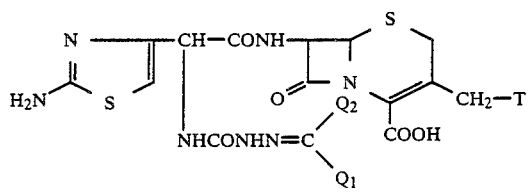

| Example | T | $Q_1$ | $Q_2$ | Yield (%) | Melting point (°C.) | $^1$HNMR($d_6$-DMSO)δ |
|---|---|---|---|---|---|---|
| 98 | [thiadiazole-S-] | [catechol] | H | 89.6 | 178° C. (decomposed) | 3.64(2H, m), 4.39(2H, m), 5.04(1H, m), 5.55(2H, m), broad absorption at 6.6–8.5 by substitution 6.86(3H, m), of deuterium 7.24(1H, d, J=8) 7.79(1H, s) 9.31(1H, d, J=8) 9.47(1H, s) |
| 99 | [N-methyl tetrazole-S-] | [catechol] | H | 94.0 | 186° C. (decomposed) | 3.72(2H, m), 3.95(3H, s), 4.34(2H, m), 5.12(1H, m), 5.68(2H, m), 6.86(1H, s), 6.7~7.5(3H, m), 7.80(1H, s) |
| 100 | [tetrazole-CH2CO2H -S-] | [catechol] | H | 98 | 140° C. (decomposed) | 3.65(2H, m), 4.35(2H, m), 5.10(1H, m), 5.33(2H, s), 5.60(2H, m), 6.56(1H, s), 6.87(2H, s), 7.19(1H, s), 7.82(1H, s) |
| 101 | [triazinone-S-] | [catechol] | H | 88 | 186° C. (decomposed) | 3.33(3H, s), 3.68(2H, m), 4.13(2H, m), 5.14(1H, m), 5.54(2H, m), 6.60(1H, s), 6.88(2H, s), 7.21(1H, s), 7.83(1H, s) |
| 102 | —OCOCH₃ | H | [catechol] | 76 | 240° C. (decomposed) | 2.01(3H, s), 3.48(2H, m), 4.4~5.2 (3H, m), 5.2~5.9(2H, m), 6.2~7.3 (4H, m), 7.60(1H, s) |
| 103 | [thiadiazole-S-] | [o-hydroxyphenyl] | —CH₃ | 83.0 | 171° C. (decomposed) | 2.32(3H, s), 3.73(2H, m), 4.46(2H, m), 5.14(1H, m), 5.66(2H, m), 6.84(2H, m), 7.1~7.7(3H, m), 9.64(1H, s) |
| 104 | [thiadiazole-S-] | [m-hydroxyphenyl] | —CH₃ | 85.0 | 167° C. (decomposed) | 2.19(3H, s), 3.70(2H, m), 4.47(2H, m), 5.14(1H, m), 5.71(2H, m), 6.90(2H, m), 7.25(3H, m), 9.62(1H, s) |
| 105 | [thiadiazole-S-] | [p-hydroxyphenyl] | —CH₃ | 84.0 | 167° C. (decomposed) | 2.19(3H, s), 3.73(2H, m), 4.48(2H, m), 5.16(1H, m), 5.22(2H, m), 6.86(2H, d, J=8), 6.94(1H, s), 7.71(2H, d, J=8), 9.65(1H, s) |

TABLE 11-continued

[Structure: A cephalosporin-type compound with aminothiazole group (H₂N—C(=S)—N=C connected to CH in ring), CH—CONH linkage, β-lactam with N-Q₂, COOH, and CH₂—T substituent on the dihydrothiazine ring. The NHCONHN=C group bears Q₁.]

| Example | T | Q₁ | Q₂ | Yield (%) | Melting point (°C.) | ¹HNMR(d₆-DMSO)δ |
|---|---|---|---|---|---|---|
| 106 | −S−(1,3,4-thiadiazol-2-yl) | 2,3-dihydroxyphenyl (OH, OH) | −CH₃ | 86.0 | 173° C. (decomposed) | 2.11(3H, s), 3.66(2H, m), 4.38(2H, m), 5.07(1H, m), 5.60(2H, m), 6.79(2H, m), 7.20(2H, m), 9.51(1H, s) |
| 107 | −S−(1,3,4-thiadiazol-2-yl) | 2,5-dihydroxyphenyl | −CH₃ | 87.0 | 170° C. (decomposed) | 2.26(3H, s), 3.73(2H, m), 4.46(2H, m), 5.14(1H, m), 5.66(2H, m), 6.6~7.2 (4H, ), 9.66(1H, s) |
| 108 | −S−(1,3,4-thiadiazol-2-yl) | 2,4-dihydroxyphenyl | −CH₃ | 87.0 | 168° C. (decomposed) | 2.27(3H, s), 3.73(2H, m), 4.49(2H, m), 5.16(1H, m), 5.67(2H, m), 6.32(2H, m), 6.78(1H, s), 7.31(1H, m), 9.57(1H, s) |
| 109 | −S−(1,3,4-thiadiazol-2-yl) | 2,3,4-trihydroxyphenyl | H | 84.5 | — | 3.70(2H, m), 4.47(2H, m), 5.14(1H, m), 5.69(2H, m), 6.40(1H, broad s), 6.88(1H, s), 7.06(1H, broad s), 8.17(1H, s), 9.62(1H, s) |
| 110 | −S−(1,3,4-thiadiazol-2-yl) | 2,3,4-trihydroxyphenyl | −CH₃ | 84.5 | 167° C. (decomposed) | 2.23(3H, s), 3.69(2H, m), 3.43(2H, m), 5.10(1H, m), 5.64(2H, m), 6.32(1H, d, J=8), 6.78(1H, s), 6.89(1H, d, J=8), 9.57(1H, s) |
| 111 | −S−(1,3,4-thiadiazol-2-yl) | H | 2-chloro-4-hydroxyphenyl (Cl, HO) | 90.5 | 162° C. (decomposed) | 3.73(2H, m), 4.48(2H, m), 5.16(1H, m), 5.74(2H, m), 6.94(1H, s), 7.05(1H, d, J=10), 7.29(dod, J=10.2), 7.88(1H, d, J=2), 8.27(1H, s) |
| 112 | −S−(1-methyl-1,2,4-triazin-3-yl with OH and =O) | 2,4-dihydroxyphenyl | H | 70 | — | 3.57(3H, s), 3.72(2H, m), 4.17(2H, m), 5.09(1H, m), 5.59(2H, m), 6.7~7.6(4H, m), 7.72(1H, s) |
| 113 | −S−(1-methyl-tetrazol-5-yl) | 2,4-dihydroxyphenyl | −CH₃ | 86 | — | 2.15(3H, s), 3.60(2H, m), 3.98(3H, s), 4.38(2H, m), 5.10(1H, m), 5.65(2H, m), 6.6~7.5(4H, m) |

EXAMPLE 114

Synthesis of 7-[2-(2-amino-1,3-thiazol-4-yl)-2-{3-(3,4-diacetoxybenzoyl)carbazoylamino}acetamido]-3-[(2-methyl-1,3,4-thiadiazol-5-yl)thiomethyl]-3-cephem-4-carboxylic acid.hydrochloride In 6 ml of dried THF were dissolved 143 mg (0.60 mmole) of 3,4-diacetoxybenzoic acid and 81 mg (0.60 mmole) of 1-hydroxybenzotriazole, the mixture was ice-cooled to maintain 0° C., and then 136 mg (0.66 mmole) of DCC was added thereto and the mixture was stirred at the same temperature for 25 minutes and at room temperature for one hour. The resulting mixture was ice-cooled to 0° C., and to the mixture was added dropwise for 5 minutes a separately prepared solution comprising 315 mg (0.500 mmole) of the compound obtained in Reference example 46 dissolved in 4 ml of DMF-0.14 ml of triethylamine. The mixture was then stirred at the same temperature for 30 minutes and at room temperature for 2 hours.

To the resulting mixture was added 25 ml of THF and the mixture was stirred for 5 minutes and filtered to remove insolubles. The filtrate was added into 150 ml of ether while stirring and after 10 minutes stirring, precipitated solids were collected by filtration. The obtained residue was washed twice with 25 ml of methylene chloride and ether, respectively, and then vacuum dried to obtain 304 mg (Yield: 75%) of a white powder of the title compound. Melting point: 123° C. (decomposed).

Structural formula:

$^1$H NMR (d$_6$-DMSO) δ: 2.30 (6H, s), 2.67 (3H, s), 3.06 (2H, m), 4.24 (2H, m), 4.9–5.7 (3H, m), 6.41 (1H, s), 7.33 (1H, d, 7.70 (2H, m).

EXAMPLE 115

Synthesis of 7-[2-(2-amino-1,3-thiazol-4-yl)-2-{3-(3,4-diacetoxybenzoyl)carbazoylamino}acetamido]-3-[(2-methyl-1,3,4-thiadiazol-5-yl)thiomethyl]-3-cephem-4-carboxylic acid.hydrochloride In 4 ml of dried methylene chloride was suspended 400 mg (0.634 mmole) of the compound obtained in Reference example 46, and to the mixture was added 1.75 ml (7.17 mmole) of N,O-bis(trimethylsilyl)acetamide and the mixture was stirred at room temperaure for 30 minutes to obtain a transparent solution. To the solution was added 202 mg (0.789 mmole) of 3,4-diacetoxybenzoylchloride at room temperature while stirring and stirring was continued at the same conditions for 45 minutes.

The resulting mixture was added into 100 ml of ether and addition of 10 ml methanol thereto under stirring caused precipitation of solids. Ten minutes later, the precipitates were collected by filtration, and the residue was washed with ether and vacuum dried to obtain 427 mg (Yield: 83%) of the title compound. This compound was accorded with the compound obtained in Example 109 in both of TLC and NMR.

EXAMPLES 116 TO 119

In the same manner as in Example 115, hydrochlo-

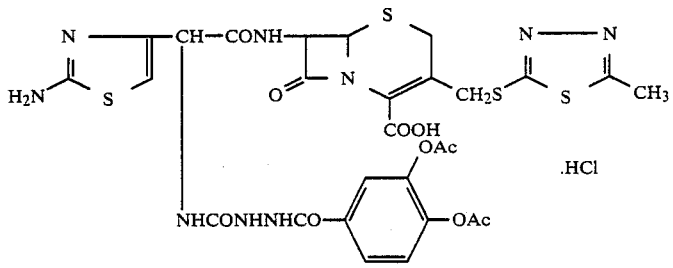

rides of the β-lactam compounds represented by the following formula were prepared. The results are shown in Table 12.

TABLE 12

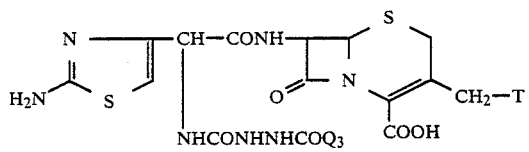

| Example | T | Q$_3$ | Yield (%) | Melting point (°C.) | $^1$HNMR(d$_6$-DMSO)δ |
|---|---|---|---|---|---|
| 116 | ![N-N thiadiazole -S-] | ![phenyl-OAc,OAc] | 89.5 | 117° C. (decomposed) | 2.30(6H, s), 3.70(2H, m), 4.42(2H, m), 5.11(1H, m), 5.67(2H, m), 6.78(1H, s), 7.34(2H, m), 7.77(1H, m), 9.54(1H, s) |

TABLE 12-continued

[Structural formula shown: cephalosporin core with H2N-C(=N)-S- thiazole-CH(NHCONHNHCOQ3)-CONH- substituent and -CH2-T at 3-position, COOH at 4-position]

| Example | T | Q3 | Yield (%) | Melting point (°C.) | ¹HNMR(d6-DMSO)δ |
|---|---|---|---|---|---|
| 117 | -S-(5-methyl-1,3,4-thiadiazol-2-yl) | 3,4-diacetoxyphenyl | 91.0 | 100° C. (decomposed) | 2.28(6H, s), 2.66(3H, s), 3.65(2H, m), 4.35(2H, m), 5.06(1H, m), 5.57(2H, m), 6.75(1H, s), 7.18(1H, broad s), 7.55(2H, broad s) |
| 118 | -S-(1,3,4-thiadiazol-2-yl) | 3,4-diacetoxyphenyl | 86.6 | 90° C. (decomposed) | 2.29(6H, s), 3.72(2H, m), 4.44(2H, m), 5.12(1H, m), 5.63(2H, m), 6.80(1H, s), 7.22(1H, m), 7.59(1H, m), 9.58(1H, s) |
| 119¹ | -S-(1,3,4-thiadiazol-2-yl) | 4-formamido-3,4-(?)-diacetoxyphenyl (-NHCO- on phenyl with OAc groups) | 72.0 | — | 2.29(6H, 2), 3.68(2H, m), 4.42(2H, m), 5.11(1H, m), 5.63(2H, m), 6.78(1H, s), 7.41(1H, m), 7.88(2H, m), 9.56(1H, s) |

Note
¹3,4-diacetoxybenzoylisocyanate was employed in place of acid chloride.

EXAMPLE 120

Synthesis of 7-[2-(2-amino-1,3-thiazol-4-yl)-2-{3-(3,4-dihydroxybenzoyl)carbazoylamino}acetamido]-3-[(2-methyl-1,3,4-thiadiazol-5-yl)thiomethyl]-3-cephem-4-carboxylic acid In 3 ml methanol solution containing 385 mg (0.474 mmole) of the compound obtained in Example 109 was added 0.38 ml of 25% aqueous ammonia and the mixture was stirred at room temperature for 2 hours. The resulting mixture was added into 100 ml of ether and the mixture was stirred for 10 minutes. Then, solids precipitated were collected by filtration, and the residue was vacuum dried to obtain 406 mg of crude powder. This powder was purified through silica gel column chromatography (Silica gel 20 g, eluent: CHCl₃—MeOH—HCOOH 50:20:6) to obtain 115 mg (Yield: 32%) of monoformix acid salt of the title compound. Melting point: 193° C. (decomposed).

Structural formula:

¹H NMR (d6-DMSO) δ: 2.68 (3H, s), 3.75 (2H, m), 4.41 (3H, m), 5.15 (1H, m), 5.57 (1H, m), 6.88 (1H, m), 7.33 (3H, m).

REFERENCE EXAMPLE 53

Synthesis of 2-(2-formylamino-1,3-thiazol-4-yl)-2-ethoxalylaminoacetic acid tert-butyl ester In 100 ml of methylene chloride was dissolved 5.5 g (21.4 mmole) of 2-amino-2-(2-formylamino-1,3-thiazol-4-yl)acetic acid tert-butyl ester, and 2.165 g (21.4 mmole) of triethylamine was added thereto. Then, the mixture was cooled to −45° C. and a solution of 2.92 g (21.4 mmole) of ethyl chlorooxalate dissolved in 10 ml of methylene chloride was added dropwise thereto for 10 minutes. Then, a cooling bath was removed, and the mixture was stirred for 30 minutes. After the mixture was washed with water, it was dried over anhydrous magnesium sulfate and the solvent was evaporated to obtain 7.5 g of the oily title compound. (Yield: 98%)

Structural formula:

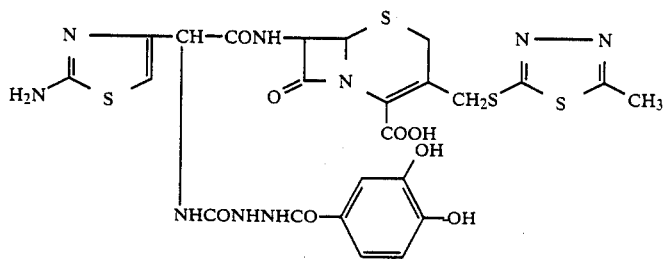

¹H NMR (CDCl₃) δ: 1.33 (t, 3H), 1.44 (s, 9H), 4.30 (q, 2H), 5.33 (d, 1H), 7.02 (s, 1H), 8.25 (d, 1H), 8.72 (s, 1H).

REFERENCE EXAMPLE 54

Synthesis of 2-(2-amino-1,3-thiazol-4-yl)-2-carbazoylcarbonylaminoacetic acid tert-butyl ester In 30 ml ethanol was dissolved 7.5 g (21.0 mmole) of 2-(2-formylamino-1,3-thiazol-4-yl)-2-ethoxalylaminoacetic acid tert-butyl ester obtained in Reference Example 53, 2.53 g (50 mmole) of hydrazine hydrate was added thereto and the mixture was refluxed for one hour. After cooling, precipitates were collected by filtration, washed with ethanol and dried to obtain 5.42 g of the title compound. (Yield: 81.8%)

Structural formula:

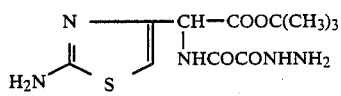

¹H NMR (d₆-DMSO) δ: 1.48 (s, 9H), 5.51 (d, 1H), 6.98 (s, 1H).

REFERENCE EXAMPLE 55

Synthesis of 2-(2-formylamino-1,3-thiazol-4-yl)-2-(3-formylcarbazoyl)carbonylaminoacetic acid tert-butyl ester After stirring of a mixed solution comprising 3 ml of anhydrous acetic acid and 1.3 ml of formix acid at 55° C. for one hour, cooled by standing, 2.73 g (8.66 mmole) of 2-(2-amino-1,3-thiazol-4-yl)-2-carbazoylcarbonylaminoacetic acid tert-butyl ester obtained in Reference example 54 was added thereto and the mixture was stirred at room temperature for 3 hours. The resulting mixture was 100 ml of diisopropyl ether to obtain powder, and the powder was collected by filtration and dried to obtain 3.15 g of the title compound. (Yield: 97.9%)

Structural formula:

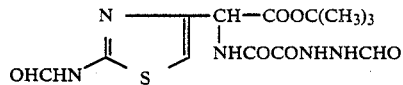

¹H NMR (d₆-DMSO) δ: 1.45 (s, 9H), 5.55 (d, 1H), 7.31 (s, 1H), 8.10 (s, 1H), 8.55 (s, 1H).

REFERENCE EXAMPLE 56

Synthesis of 2-(2-formylamino-1,3-thiazol-4-yl)-2-(3-formylcarbazoyl)carbonylaminoacetic acid In 20 ml of trifluoroacetic acid was dissolved 3.91 g (10.5 mmole) of 2-(2-formylamino-1,3-thiazol-4-yl)-2-(3-formylcarbazoyl)carbonylaminoacetic acid tert-butyl ester obtained in Reference example 55 and the mixture was stirred at room temperature for 3 hours.

The resulting mixture was added dropwise into 250 ml of ether while vigorously stirring, and resulting precipitates were collected by filtration, washed with ether and dried to obtain 3.21 g of the title compound. (Yield: 97.0%)

Structural formula:

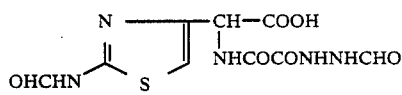

¹H NMR (d₆-DMSO) δ: 5.56 (d, 1H), 7.34 (s, 1H), 8.12 (s, 1H), 8.53 (s, 1H).

REFERENCE EXAMPLE 57

Synthesis of 7-[2-(2-formylamino-1,3-thiazol-4-yl)-2-(3-formylcarbazoyl)carbonylaminoacetamido]-3-[(1,3,4-thiadiazol-2-yl)thiomethyl]-3-cephem-4-carboxylic acid diphenylmethyl ester In 30 ml of DMF were dissolved 3.1 g (9.8 mmole) of 2-(2-formylamino-1,3-thiazol-4-yl)-2-(3-formylcarbazoyl)carbonylaminoacetic acid obtained in Reference example 56 and 4.867 g (9.8 mmole) of 7-amino-3-[(1,3,4-thiadiazol-2-yl)thiomethyl]-3-cephem-4-carboxylic acid diphenylmethyl ester, and to the mixture was added under ice-cooling and stirring 2.476 g (12 mmole) of DCC and the mixture was stirred for 30 minutes under ice-cooling and further for one hour at room temperature.

After filtration of the resulting mixture, to the filtrate was added the same amount of chloroform and the mixture was added dropwise into 700 ml of ether while vigorously stirring. Resulting precipitates were collected by filtration, washed with ether and dried to obtain 5.49 g of the title compound. (Yield: 70.6%)

Structural formula:

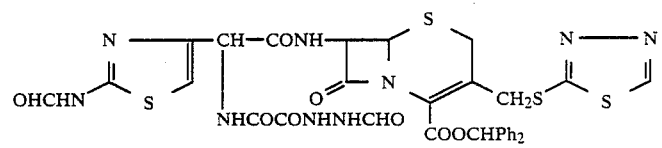

¹H NMR (d₆-DMSO) δ: 4.47 (m, 2H), 5.13 (d, 1H), 5.49–5.86 (m, 2H), 7.38 (broad s, 11H), 8.15 (s, 1H), 8.54 (s, 1H), 9.61 (s, 1H).

REFERENCE EXAMPLE 58

Synthesis of
7-[2-(2-amino-1,3-thiazol-4-yl)-2-carbazoylcarbonylaminoacetamido]-3-[(1,3,4-thiadiazol-2-yl)thiomethyl]-3-cephem-4-carboxylic acid diphenylmethyl ester.dihydrochloride Methanol (100 ml) was ice-cooled and 2.15 g of phosphorus oxychloride was added dropwise under stirring. To this mixture was added 5.49 g (6.91 mmole) of 7-[2-(2-formylamino-1,3-thiazol-4-yl)-2-(3-formylcarbazoyl)carbonylaminoacetamido]-3-[(1,3,4-thiadiazol-2-yl)thiomethyl]-3-cephem-4-carboxylic acid diphenylmethyl ester obtained in Reference example 57, and the mixture was stirred for 3 hours under ice-cooling.

After filtration of the resulting mixture, the filtrate was added dropwise into 700 ml of ether while vigorously stirring and precipitates were collected by filtration, washed with ether and dried to obtain 3.75 g of the title compound. (Yield: 66.9%).

Structural formula:

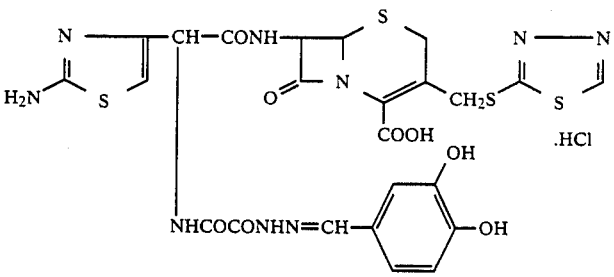

$^1$H NMR (d$_6$-DMSO) δ: 4.48 (m, 2H), 5.15 (d, 1H), 5.50–5.88 (m, 2H), 7.36 (broad s, 11H), 9.58 (s, 1H).

EXAMPLE 121

Synthesis of
7-[2-(2-amino-1,3-thiazol-4-yl)-2-{3-(3,4-dihydroxybenzylidene)carbazoylcarbonylamino}acetamido]-3-[(1,3,4-thiadiazol-2-yl)thiomethyl]-3-cephem-4-carboxylic acid.hydrochloride In 20 ml of methanol was dissolved 0.81 g (1 mmole) of 7-[2-(2-amino-1,3-thiazol-4-yl)-2-carbazoylcarbonylaminoacetamido]-3-[(1,3,4-thiadiazol-2-yl)thiomethyl]-3-cephem-4-carboxylic acid diphenylmethyl ester dihydrochloride obtained in Reference example 58, and 0.138 g (1 mmole) of 3,4-dihydroxybenzaldehyde was added thereto and the mixture was stirred at room temperature for one hour. After filtration of the resulting mixture, the filtrate was added dropwise into 250 ml of ether while vigorously stirring, and precipitates were collected by filtration, washed with ether and then dried to obtain 0.78 g of diphenylmethyl ester of the title compound. (Yield: 87.2%)

After a mixed solution comprising 4 ml of trifluoroacetic acid and 1 ml of anisole was ice-cooled, 0.47 g (0.525 mmole) of the previously obtained diphenylmethyl ester was added thereto and the mixture was stirred for 30 minutes under ice-cooling. This mixture was added dropwise into 100 ml of ether while vigorously stirring and precipitates were collected by filtration, washed with ether and then dried to obtain 0.375 g of the title compound. (Yield: 98.1%)

Melting point: 240° C. (decomposed)
Structural formula:

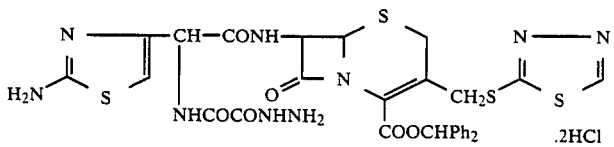

$^1$H NMR (d$_6$-DMSO) δ: 4.50 (m, 2H), 5.15 (d, 1H), 5.55–5.87 (m, 2H), 6.70–7.55 (m, 4H), 8.48 (m, 1H), 9.61 (s, 1H).

REFERENCE EXAMPLE 59

Synthesis of
2-(2-formylamino-1,3-thiazol-4-yl)-2-carbazoylaminoacetic acid ethyl ester.trifluoroacetic acid salt After a mixture comprising 30 ml of trifluoroacetic acid and 10 ml of anisole was ice-cooled, 3.87 g (10 mmole) of the compound of Reference example 27 was added thereto while stirring and the mixture was stirred at the same temperature for 30 minutes and at room temperature for 18 hours. The resulting mixture was added dropwise into a mixed solution comprising 100 ml of ether and 150 ml of diisopropyl ether while stirring, and precipitated crystals were collected by filtration and vacuum dried to obtain 3.82 g (Yield: 95.2%) of a white crystal of the title compound.

Structural formula:

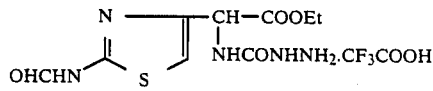

$^1$H NMR (d$_6$-DMSO) δ: 1.17 (3H, t, J=8), 4.12 (2H, q, J=8), 5.43 (1H, d, J=9), 7.23 (1H, s), 8.49 (1H, s).

REFERENCE EXAMPLE 60

Synthesis of
2-(2-amino-1,3-thiazol-4-yl)-2-carbazoylaminoacetic acid ethyl ester.dihydrochloride In 30 ml of ethanol was added under ice-cooling 1.77 ml (19.04 mmole) of phosphorus oxychloride, and after the mixture was stirred for 5 minutes, 3.82 g (9.52 mmole) of the compound according to Reference example 59 was added thereto at the same temperature and the mixture was stirred for 2 hours. The resulting mixture was added dropwise into 500 ml of ether while stirring, and precipitated crystals were collected by filtration and dried to obtain 2.45 g (Yield: 77.6%) of the title compound as dihydrochloride.

Structural formula:

Melting point: 155° C. (decomposed)

¹H NMR (d₆-DMSO) δ: 1.20 (3H, t, J=8), 4.15 (2H, q, J=8), 3.46 (1H, d, J=9), 6.80 (1H, s).

REFERENCE EXAMPLE 61

Synthesis of 2-(amino-1,3-thiazol-4-yl)-2-[3-(3,4-diacetoxybenzoyl)-carbazoylamino]acetic acid ethyl ester.hydrochloride After 2.45 g (7.37 mmole) of the compound according to Reference example 60 was suspended in 40 ml of methylene chloride, 9.01 ml (36.85 mmole) of N,O-bis(-trimethylsilyl)acetamide was added thereto and the mixture was stirred for 30 minutes whereby the starting materials were dissolved completely. To the mixture was added 2.10 g (8.18 mmole) of crystals of 3,4-diacetoxybenzoyl chloride and the mixture was stirred at room temperature for 50 minutes. After the mixture was added into 400 ml of diisopropyl ether, 20 ml of methanol was added thereto while stirring so that white crystals were precipitated at once. These crystals were collected by filtration and vacuum dried to obtain 6.02 g of hydrochloride of the title compound containing acetamide. This compound was employed for the next reaction without further drying.

Structural formula:

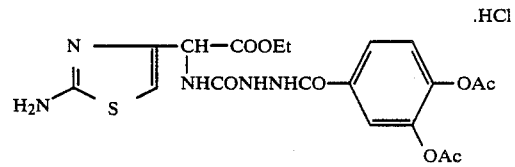

NMR (d₆-DMSO) δ: 1.20 (3H, t, J=8), 1.82 (about 10H, s; acetylmethyl protons of acetamide), 3.29 (6H, s), 4.14 (2H, q, J=8), 5.47 (1H, broad s, J=8), 6.80 (1H, s), 7.38 (1H, d, J=8), 7.79 (1H, s), 7.86 (1H, d, J=8).

REFERENCE EXAMPLE 62

Synthesis of 2-(2-amino-1,3-thiazol-4-yl)-2-[3-(3,4-dihydroxybenzoyl)carbazoylamino]acetic acid In 37 ml of 1N aqueous sodium hydroxide solution was dispersed 6.02 g of crystals of 2-(2-amino-1,3-thiazol-4-yl)-2-[3-(3,4-diacetoxybenzoyl)carbazoylamino]acetic acid ethyl ester.hydrochloride containing acetamide according to Reference example 61, and the mixture was stirred at room temperature for 1.5 hours. During stirring, crystals were dissolved completely. To this mixture was added 2N hydrochloric acid while stirring, and pH of the mixture was adjusted to 3.5. After further stirring for 10 minutes, precipitated crystals were collected by filtration, and the residue was washed well with water and vacuum dried over phosphorus pentoxide to obtain 1.36 g (Yield: 50.2%) of pale yellow crystals of the title compound.

Melting point: 197° C. (decomposed).

Structural formula:

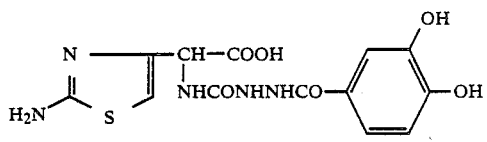

¹H NMR (d₆-DMSO) δ: 4.48 (1H, s), 6.79 (2H, broad s, J=9), 7.31 (3H, m).

EXAMPLE 122

Synthesis of 7-[2-(2-amino-1,3-thiazol-4-yl)-2-{3-(3,4-dihydroxybenzoyl)carbazoylamino}acetamido]-3-[(2-methyl-1,3,4-thiadiazol-5-yl)thiomethyl]-3-cephem-4-carboxylic acid diphenylmethyl ester In 9 ml of dried dimethylformamide was dissolved a mixture comprising 1.00 g (2.72 mmole) of the compound obtained in Reference example 62 and 1.39 g (2.72 mmole) of 7-amino-3-(2-methyl-1,3,4-thiadiazol-5-yl)thiomethyl-3-cephem-4-carboxylic acid diphenylmethyl ester, and 0.674 g (3.27 mmole) of DCC was added thereto under ice-cooling and stirring and the mixture was stirred at the same temperature for 30 minutes and at room temperature for 18 hours. After filtration of the mixture and the residue was washed with a small amount of dimethylformamide, the filtrate and washing were combined and added dropwise into 250 ml of ether while stirring. After 10 minutes stirring, precipitated solid was collected by filtration, washed well with ether and vacuum dried to obtain 1.96 g (Yield: 84%) of pale yellow powder of the title compound.

Melting point: 150° C. (decomposed).

Structural formula:

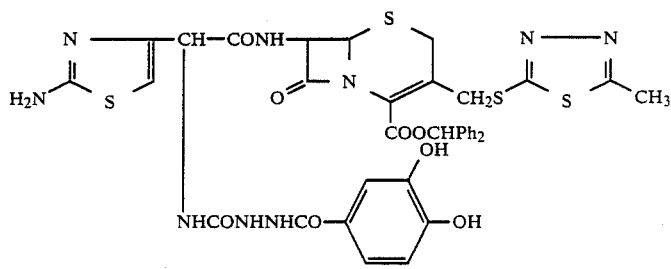

¹H NMR (d₆-DMSO) δ: 2.63 (3H, s), 3.73 (2H, m), 4.35 (2H, m), 5.0–5.9 (3H, m), 6.92 (12H, m), 7.41 (13H, m).

EXAMPLE 123

Synthesis of 7-[2-(2-amino-1,3-thiazol-4-yl)-2-{3-(3,4-dihydroxybenzoyl)carbazoylamino}acetamido]-3-[(2-methyl-1,3,4-thiadiazol-5-yl)thiomethyl]-3-cephem-4-carboxylic acid.ditrifluoroacetic acid salt To 300 mg (0.349 mmole) of the compound according to Example 117 were added successively 1 ml of anisole and 5 ml of trifluoroacetic acid and the mixture was stirred under ice-cooling for one hour. The reaction mixture was added dropwise into 100 ml ether while stirring, and precipitated solids were collected by filtration, washed with ether and vacuum dried to obtain 295 mg (Yield: 91.7%) of ditrifluoroacetic acid salt of the title compound as a pale yellow powder. This compound was confirmed that NMR data thereof were accorded with those of the compound obtained in Example 115.

REFERENCE EXAMPLE 63

The minimum inhibition concentrations (MIC) of the compounds obtained by the present invention were measured according to the standard method of Japanese Chemotherapy Association. The results are shown in Tables 13 and 14.

In Table 13, As comparative compounds, cephotaxim (abbreviated to as CTX), cephazoline (abbreviated to as CAZ), cephothiam (abbreviated to as CTM) and latamoxiceph (abbreviated to as LMOX) were used.

TABLE 14

| Strain | MIC (μg/ml) Example No. | |
|---|---|---|
| | 104 | 118 |
| E. Coli GN5482 | 0.78 | 1.56 |
| E. cloacae GN7471 | 3.13 | 6.25 |
| C. freundii GN7391 | 100 | >100 |
| S. marcescens GN10851 | 100 | 100 |
| P. rettgeri GN4430 | 0.2 | 0.39 |
| P. morganii GN5407 | 0.39 | 0.78 |
| P. vulgaris GN7919 | 50 | 100 |
| P. aeruginosa GN10 | 6.25 | 6.25 |
| E. coli W3630/Rms212 | 0.39 | 0.39 |
| E. coli W3630/Rms213 | 0.1 | 0.2 |
| E. coli W3630/Rte16 | 0.2 | 0.39 |

We claim:

1. A β-lactam compound represented by the formula:

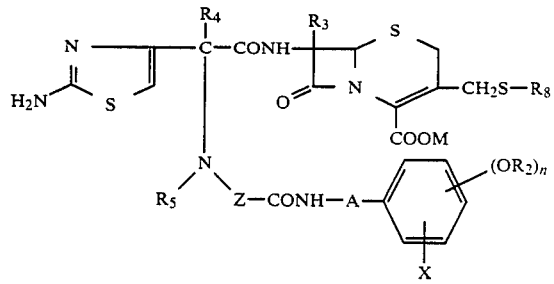

wherein A is a group represented by the formula —NHCO—, —NHCONHCO—, —NHCOCH=CH— or

TABLE 13

| Strain | MIC (μg/ml) | | | | | | |
|---|---|---|---|---|---|---|---|
| | Example 2 | Example 59 | Example 62 | CTX | CAZ | LMOX | CTM |
| S. aureus TASAKI | 1.56 | 1.56 | 1.56 | 1.56 | 12.5 | 3.13 | 0.39 |
| S. aureus 209P JC-1 | 0.78 | 0.39 | 0.39 | 0.39 | 0.78 | 3.13 | 0.2 |
| S. aureus ATCC25923 | 0.78 | 0.78 | 0.39 | 0.78 | 12.5 | 3.13 | 0.39 |
| S. aureus Smith | 3.13 | 0.78 | 3.13 | 3.13 | 6.25 | 6.25 | 0.39 |
| S. epidermidis ATCC14990 | 0.78 | 0.39 | 0.39 | 0.78 | 6.25 | 6.25 | 0.39 |
| S. faecalis IFO3826 | >100 | >100 | >100 | >100 | >100 | >100 | >100 |
| B. subtilis ATCC6633 | 0.39 | 0.39 | 0.39 | 0.39 | 6.25 | 3.13 | 0.39 |
| S. anatum 677-69 | 0.05 | 0.025 | 0.025 | 0.1 | 0.78 | 0.1 | 0.2 |
| S. newport 563 | 0.05 | 0.05 | 0.05 | 0.1 | 0.78 | 0.1 | 0.39 |
| S. paratyphi A 144-12-93 | 0.05 | 0.025 | 0.025 | 0.2 | 1.56 | 0.2 | 0.39 |
| S. paratyphi B | 0.025 | 0.012 | 0.012 | 0.1 | 0.78 | 0.05 | 0.2 |
| S. paratyphi C 33-76 | 0.012 | 0.012 | 0.012 | ≦0.006 | 0.1 | 0.025 | 0.05 |
| S. typhi 1099-77 | ≦0.006 | ≦0.006 | ≦0.006 | 0.1 | 0.39 | 0.05 | 0.1 |
| S. typhimurium ATCC13311 | 0.05 | 0.1 | 0.025 | 0.05 | 0.39 | 0.05 | 0.1 |
| S. typhimurium IFO 12529 | 0.39 | 0.1 | 0.05 | 0.2 | 0.78 | 0.1 | 0.2 |
| S. boyadii CDC⊕2064-59 | 0.78 | 0.39 | 0.39 | 0.39 | 6.25 | 3.13 | 0.39 |
| S. dysenteriae 4379-60 | 0.025 | 0.05 | 0.025 | 0.012 | 0.2 | 0.05 | 0.05 |
| S. flexneri 2a CDC⊕4807-62 | 0.1 | 0.2 | 0.1 | 0.025 | 0.2 | 0.1 | 0.1 |
| S. flexneri Y NCTC⊕9730 | 0.78 | 0.78 | 0.78 | 0.05 | 0.39 | 3.13 | 0.78 |
| S. sonnei SH72-415 | 0.05 | 0.05 | 0.05 | 0.05 | 0.39 | 0.1 | 0.2 |
| E. coli ATCC25922 | 0.2 | 0.1 | 0.2 | 0.1 | 0.39 | 0.2 | 0.2 |
| E. coli NIHJ JC-2 | 0.39 | 0.39 | 0.78 | 0.1 | 0.78 | 0.2 | 0.2 |
| C. freundii IFO12681 | 0.39 | 0.78 | 0.39 | 0.1 | 0.39 | 0.1 | 3.13 |
| S. marcescens IFO12648 | 0.39 | 0.39 | 0.39 | 0.2 | 0.39 | 0.2 | 6.25 |
| E. cloacae ATCC13047 | 3.13 | 1.56 | 3.13 | 3.13 | 3.13 | 0.78 | 50 |
| K. pneumoniae ATCC27736 | 0.025 | 0.012 | 0.012 | 0.1 | 0.78 | 0.05 | 0.1 |
| P. mirabilis IFO3849 | 0.2 | 0.39 | 0.39 | 0.05 | 0.2 | 0.1 | 0.78 |
| P. rettgeri ATCC14505 | 0.39 | 0.78 | 1.56 | 0.1 | 0.39 | 0.1 | 3.13 |
| P. vulgaris ATCC6380 | 0.2 | 0.39 | 0.39 | 0.05 | 0.2 | 0.2 | >100 |
| P. vulgaris ATCC6398 | 0.05 | 0.05 | 0.05 | ≦0.006 | 0.1 | 0.2 | >100 |
| P. aeruginosa ATCC9721 | 0.2 | 0.1 | 0.1 | 3.13 | 1.56 | 3.13 | >100 |
| P. cepacia ATCC25416 | 0.78 | 0.39 | 0.78 | 0.78 | 6.25 | 6.25 | 0.39 |
| P. maltophilia ATCC13637 | 1.56 | 0.78 | 1.56 | 50 | 12.5 | 25 | >100 |
| P. putida ATCC12633 | 1.56 | 0.78 | 1.56 | 50 | 12.5 | 25 | >100 |
| P. fluorescens ATCC13525 | 12.5 | 12.5 | 12.5 | 25 | 3.13 | | |

where $R_6$ is a hydrogen atom or a lower alkyl group; $R_2$ is independently a hydrogen atom, a lower alkanoyl group, or a lower alkoxy carbonyl group; $R_3$ is a hydrogen atom or a methoxy group; X is a hydrogen atom, a hyroxyl group, a lower alkonoyloxy group, a lower alkoxy carbonyloxy group, a halogen atom, a lower alkoxy group or a nitro group; n is an integer of 1 or 2; M is a hydrogen atom, a protective group selected from the group consisting of a diphenylmethyl group, a t-butyl group, a p-nitrobenzyl group and a trimethylsilyl group or an easily hydrolyzable group in a human body selected from the group consisting of an acetoxymethyl group, an α-acetoxethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group; $R_8$ is an unsubstituted 5- to 6-membered nitrogen and/or sulfur-containing heterocyclic group having 1–4 hetero atoms in a ring or a 5- or 6-membered, nitrogen-containing heterocyclic group having 1 to 4 hetero atoms in a ring substituted by at least one of lower alkyl, lower alkoxy, carboxy-lower alkyl, sulfoxyl-lower alkyl, di-lower alkyl amino-lower alkyl, carboxy, amino, lower alkanoyl amino, or hydroxy lower alkyl group, $R_4$ and $R_5$ are each hydrogen atoms or combined with each other to form additional direct bond; Z is a direct bond or a carbonyl group when $R_4$ and $R_5$ are hydrogen atoms, or a formula: —O—B— where the oxygen atom is bonded to nitrogen atom and B is a straight, branched or cyclic alkylene group when $R_4$ and $R_5$ are combined with each other to form additional direct bond, or its pharmaceutically acceptable salt.

2. A β-lactam compound according to claim 1, wherein said lower alkyl group of $R_6$ is a straight or branched alkyl group having 1 to 3 carbon atoms.

3. A β-lactam compound according to claim 1, wherein said lower alkoxy group of X is a alkoxy group having 1 to 6 carbon atoms.

4. A β-lactam compound according to claim 1, wherein M is said protective group selected from the group consisting of a diphenylmethyl group, a t-butyl group, a p-nitrobenzyl group and a trimethylsilyl group.

5. A β-lactam compound according to claim 1, wherein M is said easily hydrolizable group in a human body selected from the group consisting of an acetoxymethyl group, an α-acetoxyethyl group, a pivaroyloxymethyl group, an α-ethoxycarbonyloxymethyl group, an α-methoxycarbonyloxymethyl group, an α-methoxycarbonyloxyethyl group, an α-ethoxycarbonyloxyethyl group, a 1-indanyl group, a phthalidyl group and a 5-methyl-2-oxo-1,3-dioxol-4-yl-methyl group.

6. A β-lactam compound according to claim 1, wherein said substituted or unsubstituted heterocyclic ring of $R_8$ is a substituted or unsubstituted tetrazolyl group, a triazolyl group, a thiazolyl group, a thiadiazolyl group, a tetrazolo[1,5-b]pyridazinyl group, a pyridyl group, an N-methylpyridyl group, an s-triazolo[1,5-a]pyrimidyl group, a 1-oxidopyridyl group, an N-carbamoylmethylpyridyl group, a 2-methyl-5-oxo-6-hydroxy-2,5-dihydro-1,2,4-triazinyl group, a 4-methyl-5-oxo-6-hydroxy-4,5-dihydroxy-1,2,4-triazinyl group.

7. A β-lactam compound according to claim 6, wherein said substituent of the heterocyclic ring of $R_8$ is selected from the group consisting of a lower alkyl group, a lower alkoxy group, a carboxymethyl group, a carboxyethyl group, a sulfoxymethyl group, a sulfoxyethyl group, a di-lower-alkylaminoethyl group, a carboxy group, an amino group, an acetylamino group and a hydroxyethyl group.

8. A β-lactam compound according to claim 1, wherein said pharmaceutically acceptable salt of the β-lactam compound is alkali metal salts; alkaline earth metal salts; ammonium salts; salts with organic bases; salts with organic acids; or salts with inorganic acids.

9. A β-lactam compound according to claim 8, wherein said pharmaceutically acceptable salt of the β-lactam compound is sodium salts, potassium salts; magnesium salts, calcium salts, salts with diisopropylamine, benzylamine, triethanolamine, triethylamine, N-methylmorpholine, pyridine, piperazine; salts with acetic acid, formic acid, maleic acid, fumaric acid, methanesulfonic acid, p-toluenesulfonic acid, hydrochloric acid, hydrobromic acid, sulfuric acid or phosphoric acid.

* * * * *